United States Patent [19]

Fair

[11] Patent Number: 5,187,155
[45] Date of Patent: Feb. 16, 1993

[54] ANTICOAGULANT PEPTIDES

[75] Inventor: Daryl S. Fair, Tyler, Tex.

[73] Assignee: Board of Regents, The University of Texas System, Austin, Tex.

[21] Appl. No.: 371,561

[22] Filed: Jun. 23, 1989

[51] Int. Cl.$^5$ .................. C07K 7/00; A61K 37/02
[52] U.S. Cl. ........................ 514/12; 530/324; 530/325; 530/326; 530/327; 530/328; 514/13; 514/14; 514/15
[58] Field of Search ............... 530/324, 328, 326, 327, 530/328; 514/12, 13, 14, 15

[56] References Cited

U.S. PATENT DOCUMENTS

| | | | |
|---|---|---|---|
| 4,533,549 | 8/1985 | Lasker | 514/56 |
| 4,622,389 | 11/1986 | Nagasawa et al. | 530/331 |
| 4,736,018 | 4/1988 | Reutelingsperger | 530/381 |
| 4,772,686 | 9/1988 | Szelke et al. | |
| 4,791,100 | 12/1988 | Kramer et al. | |

OTHER PUBLICATIONS

Leytus et al., Proc. Natl. Acad. Sci., vol. 81, pp. 3699–3702, Jun. 1984.
Chattopadhyay et al., J. Biol. Chem., vol. 264, No. 19, pp. 11035–11043, Jul. 1989.
Fung et al., Proc. Natl. Acad. Sci., vol. 82, pp. 3591–3595, Jun. 1985.
McMullen et al., Biochemistry, vol. 22, No. 12, pp. 2875–2884, 1983.
Nawroth et al.; *Thrombosis Research* 44:625–637 (1986).
Wildgoose and Kisiel; *Biochem. Biophys. Res. Commun.* 152(3):1207–1212 (1988).
Glen et al.; *Peptide Research* 1(2):65–73 (1988).
Dialog Search Report.

*Primary Examiner*—Lester L. Lee
*Assistant Examiner*—A. M. Davenport
*Attorney, Agent, or Firm*—Arnold, White & Durkee

[57] ABSTRACT

A number of novel anticoagulant peptides are claimed. These include V-V-I-K-H-N-R-F-T-K-E-T-Y-D-F-D-I, A-V-L-R-L-K-T-P-I-T-F-R-M-N-V-A-P-A-C-L, A-F-L-K-W-I-D-R-S-M-K-T-R-G-L, T-E-Q-E-E-G-G-E-A-V-H-E-V-E-V-V-I-K, L-L-I-N-E-E-N-E-G-F-G-G, C-L-Y-Q-A-K-R-F-K-V-R-V-G-D-R-N-T-E-Q-E-E-G-G-E-A-V, E-Q-E-E-G-G-E-A-V-H-E-V-E-V-V-I, and F-C-A-G-Y-T-D-K-Q-E-D-A-C and their analogues are claimed. The peptides are useful for inhibiting activation of Factor X and/or function of Factor Xa.

19 Claims, 9 Drawing Sheets

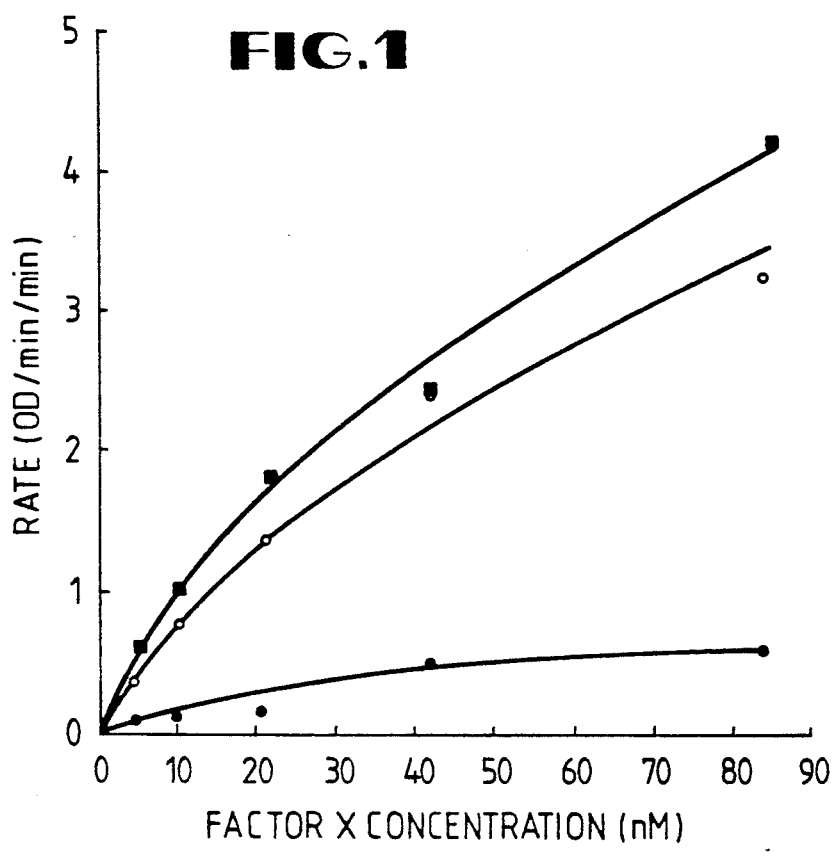
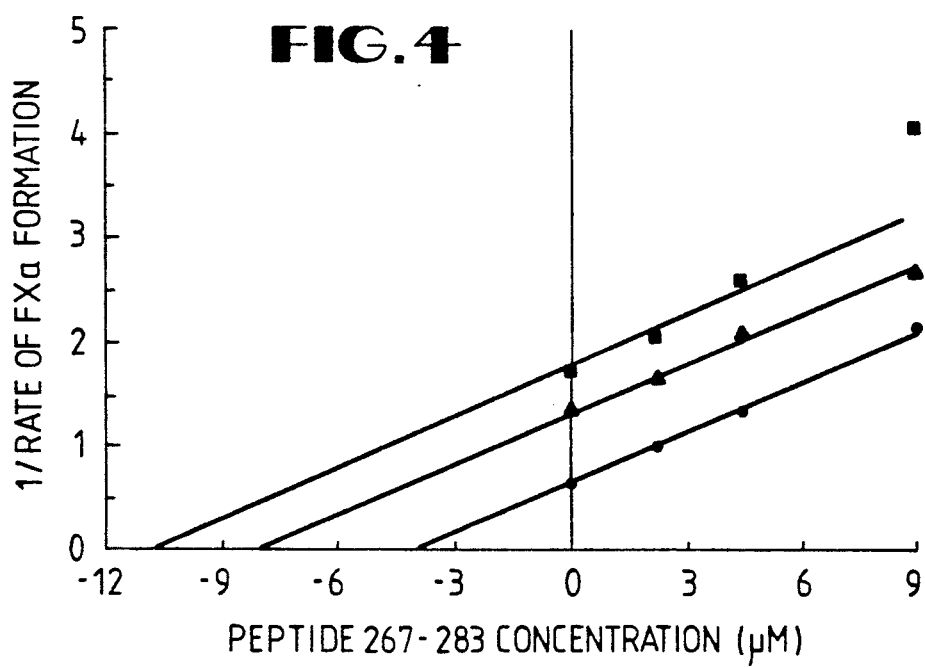

ANTICOAGULANT PEPTIDES

The development of this invention was aided by a research grants HL 39040 and HL 37770 from the National Institutes of Health. Accordingly, the Government may own certain rights.

FIELD OF THE INVENTION

The present invention relates to novel peptide agents, useful as pharmaceutical agents for preventing blood clot formation. The invention also includes pharmaceutical compositions comprising such compounds.

BACKGROUND OF THE INVENTION AND DESCRIPTION OF RELATED ART

Anticoagulants are used in the treatment of a wide variety of thrombotic disorders and in the laboratory to prevent the clotting of conserved blood. Heparin, for example, is widely used against thrombosis, but it carries a high risk of hemorrhage or thrombocytopenia, is ineffective in many conditions, and may produce unpredictable results including recurrent thromboembolism. Derivatives of 4-hydroxycoumarin or of 1,4 idanedione also have a number of disadvantages. It is very difficult to maintain a therapeutic dose due to wide variability in patient's diet, effective drug dosage, and drug metabolism. Hemorrhage is a common complication and treatment of this side effect requires the use of potentially hazardous (virus containing) plasma.

Other anticoagulants include those endogenous to the plasma, for example, antithrombin III, and proteins obtained from certain plants and organisms, including the leech-derived polypeptides prvded by U.S. Pat. No. 4,971,100 and the Kunitz inhibitor obtained from soybean. The latter blocks the blood coagulation cascade by inhibition of activated Factor X, but the specificity of the inhibitor is so low that many side effects develop, including for example, inhibition of plasma kallikrein, plasmin and trypsin. Other active compounds, such as the Ascaris or Kazals inhibitor have also been criticized for their lack of specificity.

The complexity of the blood-clotting system exacerbates the need for an acceptable pharmaceutical agent capable of inhibiting coagulation at a specifically defined point in the pathway. Clotting results from a complex series of interactions, which culminate in the thrombin-mediated cleavage of fibrinogen to fibrin and its subsequent crosslinking. Thrombin production may result from either of two systems, an "intrinsic" system based on circulating blood components and an "extrinsic" system requiring a tissue component. In each system, there is a cascade of reactions during which each of a series of inactive factors is converted by a proteolytic reaction into the corresponding active or "a" Factor that is itself a proteolytically active enzyme or a nonproteolytic active cofactor effecting the next step.

In the intrinsic system, circulating Factor XII (Hageman Factor) is postulated to bind to damaged surfaces or aggregated platelets. Kallikrein cleaves it to form Factor XIIa. Factor XIIa, in the presence of high molecular weight kininogen, 1) cleaves circulating Factor XI (plasma thromboplastin antecedent) to Factor XIa (plasma thromboplastin) and 2) cleaves circulating prekallikrein to active kallikrein, effecting amplification of the pathway. Factor XIa, in the presence of calcium ions, cleaves circulating Factor IX (Christmas Factor) to Factor IXa. Factor IXa, with circulating Factor VIII (antihemophilic globulin or AHG) in the presence of calcium ions and cell-derived phospholipid, forms a lipoprotein complex with circulating Factor X and cleaves it to form Factor Xa. Thus, in the intrinsic system, activation of Factor X requires the interaction of Factor IXa (enzyme) and Factor VIIIa (non-proteolytic cofactor) on a phospholipid surface in the presence of calcium ion.

In the extrinsic system, Factor VII associates with a tissue lipoprotein called tissue thromboplastin or tissue factor (Factor III) and in the presence of calcium ions, forms a complex with circulating Factor X and cleaves it to form a second source of Factor Xa. Factor Xa cleaves tissue factor-bound Factor VII to Factor VIIa, a much more active enzyme, thus amplifying the effects of this pathway. Factor IX may also be converted to Factor IXa by Factor VIIa and tissue factor further amplifying factor Xa formation through the "intrinsic" pathway. Thus, the extrinsic Factor X activation complex is composed of Factor VII/VIIa (enzyme) assembled with the integral membrane-bound non-proteolytic cofactor, tissue factor, in the presence of calcium. The extrinsic pathway of activation is probably the physiologically relevant system, as patients deficient in Factor XII, prekallikrein or high molecular weight kininogen do not have a bleeding disorder. Deficiencies in the other blood coagulation components all may lead to hemophilia.

Factor X may also be converted to an active serine protease upon cleavage by a specific enzyme from Russell's viper venom (RVV-X) in the presence of calcium ions.

Factor X plays a pivotal role in the coagulation scheme; its activation occurs at the point of convergence of the extrinsic and intrinsic activation pathways (1). Factor Xa, with activated Factor V and in the presence of calcium ions and cellular phospholipid, forms a lipoprotein complex with Factor II (prothrombin) and cleaves it to form thrombin (Factor IIa). In other words, activated Factor Xa (enzyme) associates with Factor Va (non-proteolytic cofactor) in a macromolecular membrane complex responsible for the activation of prothrombin.

Thrombin converts circulating fibrinogen to the insoluble form fibrin, which spontaneously polymerize into filaments and is then cross-linked under the action of Factor XIIIa, an enzyme formed from Factor XIII by thrombin activation.

As indicated above, because of the complexity of the system, the preferred anticoagulant is one that can be specifically targeted to selected steps in the coagulation cascade. However, as stated above, in the past, such agents were not available or suffered from serious drawbacks, such as their toxicity or their antigenicity in humans.

SUMMARY OF THE INVENTION

Therefore, the present inventor has now provided a number of novel anticoagulant peptides that can be specifically targeted to selected steps in the coagulation cascade and overcome the disadvantages of the type set forth above.

In its most general sense, the invention comprises anticoagulant peptides capable of inhibiting intrinsic or extrinsic pathway mediated activation of Factor X by at least 40%. Preferably, the test conditions will be similar to those set forth in the Examples, and more preferably to those set forth in Table 1. Using those conditions, one of ordinary skill-in-the-art can determine percent of inhibition as described herein.

The inventor has also discovered anticoagulant peptides that directly inhibit the rate of thrombin formation and, accordingly, claims a peptide capable of inhibiting the rate of thrombin formation by at least 40%. Preferably, the test conditions will be those set forth in Table 1a and the Examples below.

An important aspect of the present invention is that peptides homologous to certain regions in the Factor X molecule—regions whose significance was not previously understood—are particularly effective inhibitors of the prothrombin activation and/or thrombin formation mediated by Factor Xa. In general, these peptides range from about 10-50 amino acids in length and have at least about 95% homology to a sequence of from about 10-50 amino acids selected from the following sequence.
E-Q-E-E-G-G-E-A-V-H-E-V-E-V-V-I-K-H-N-R-F-T--K-E-T-Y-D-F-D-I-A-V-L-R-L-K-T-P-I-T-F-R-M-N-V-A-P-A-C-L. For the purposes of the present invention, amino acid homology may be determined by methods known to those of skill in the art, for example, by the method utilized by McLachlin, A. D. (1971) *J. Mol. Biol.* 61:409-424.

The inventor has also discovered a series of peptides capable of inhibiting activation of Factor X. Such peptides have a sequence that is at least about 95% homologous to a sequence of from about 15-35 amino acids selected from the following sequence V-V-I-K-H-N-R-F-T-K-E-T-Y-D-F-D-I-A-V-L-R-L-K-T-P-I-T-F-R-M-N-V-A-P-A-C-L.

A more preferred embodiment of the invention includes peptides ranging from about 14-20 amino acids in length characterized by their homology to particular selected sequences. For example, the invention comprises a peptide of from about 14-20 amino acids that contains a stretch of amino acids exhibiting at least about 95% amino acid homology to a peptide sequence V-V-I-K-H-N-R-F-T-K-E-T-Y-D-F-D-I. In yet another preferred embodiment, the peptide will comprise about 14-20 amino acids and contain a stretch of amino acids exhibiting at least about 95% homology to the following peptide, A-V-L-R-L-K-T-P-I-T-F-R-M-N-V-A-P-A-C-L. A third preferred embodiment comprises a peptide of about 14-20 amino acids which contains a stretch of amino acids exhibiting at least about 95% homology to the sequence A-F-L-K-W-I-D-R-S-M-K-T-R-G-L. A fourth preferred peptide comprises about 14-20 amino acids and contains a stretch of amino acids exhibiting at least about 95% homology to a peptide sequence T-E-Q-E-E-G-G-E-A-V-H-E-V-E-V-V-I-K. A fifth preferred peptide comprises about 12 to 20 amino acids and contains a stretch of amino acids exhibiting at least about 95% homology to a peptide sequence L-L-I-N-E-E-N-E-G-F-G-G. A sixth preferred peptide comprises about 16 to 30 amino acids and contains a stretch of amino acids exhibiting at least about 95% homology to a peptide sequence C-L-Y-Q-A-K-R-F-K-V-R-V-G-D-R-N-T-E-Q-E-E-G-G-E-A-V. Yet another preferred peptide comprises about 14 to 20 amino acids and contains a stretch of amino acids exhibiting at least about 95% homology to a peptide sequence E-Q-E-E-G-G-E-A-V-H-E-V-E-V-V-I. Yet another peptide that is preferred comprises about 10 to 16 amino acids and contains a stretch of amino acids exhibiting at least about 95% nomology to a peptide sequence F-C-A-G-Y-T-D-K-Q-E-D-A-C.

The invention also comprises a number of peptides having specific amino acid sequences: These sequences include V-V-I-K-H-N-R-F-T-K-E-T-Y-D-F-D-I, A-V-L-R-L-K-T P-I-T-F-R-M-N-V-A-P-A-C-L, A-F-L-K-W-I-D-R-S-M-K-T-R-G-L, T-E-Q-E-E-G-G-E-A-V-H-E-V-E-V-V-I-K, L-L-I-N-E-E-N-E-G-F-G-G, C-L-Y-Q-A-K-R-F-K-V-R-V-G-D-R-N-T-E-Q-E-E-G-G-E-A-V, E-Q-E-E-G-G-E-A-V-H-E-V-E-V-V-I and F-C-A-G-Y-T-D-K-Q-E-D-A-C.

Each peptide of the present invention will generally include less than about a hundred amino acids, preferably from about 10-50 amino acids, and most preferably from about 14-35 amino acids. The peptides may be prepared using any of a number of methods known to those of skill in the art. Synthetic peptide synthesis is preferred as such synthesis automatically yields a substantially purified preparation of peptide which may be incorporated into pharmaceutical preparations and other compositions for use in treatment of individuals without the need for the extensive purification procedures that would be required to separate peptides from a complex protein mixture such as plasma. Once the peptides of the present invention have been prepared, they may be formulated into a pharmaceutical preparation for the treatment of clotting disorders and other conditions where anticoagulant therapy is warranted, e.g., deep vein thrombosis, pulmonary embolism, or disseminated intravascular coagulation.

The peptides may be administered directly or formulated together with any pharmaceutical vehicle, including, for example, water, oil, water and oil emulsions, peptide in oil suspensions, and any other suitable pharmaceutical formulations known to those of skill in the art. In a preferred embodiment, the peptide will comprise at least 0.05% to 5.0% of the formulation by weight per unit volume.

Also included within the scope of the invention are methods for using the peptides to treat individuals most preferably, those having clotting disorders. Generally, the peptides will be administered by parenteral mode. However, alternative methods of administration may be used.

Finally, the invention includes a number of immunoglobulin preparations, wherein the antibodies or immunoglobulin molecules contained in such preparations are immunologically specific for (or immunologically reactive with) the peptides of the present invention.

These and other aspects of the present invention will become more readily apparent when viewed in the context of the description of specific embodiments and the examples set below. However, neither the summary, the description, or the examples are intended to limit the scope of the claims unless expressly stated herein.

DESCRIPTION OF THE DRAWINGS

FIG. 1. The effect of selected synthetic peptides of Factor X on the rate of Factor Xa formation as a function of the concentration of Factor X. The extrinsic activation complex (0.2% tissue factor, 0.15 nM Factor VII, 4 mM $CaCl_2$) was incubated with buffer (closed square) or 400 uM of peptide 253-270 (open circle) or 267-283 (closed circle) for 30 min at 37 degrees Centigrade in order to reach equilibrium for the peptide-protein interactions. Factor X was added (5.25-84 nM), aliquots of the reactions were withdrawn at various times and the rate of Factor Xa generation was measured in an kinetic chromogenic assay (OD 405/min/-min).

FIG. 4. Dixon plot of the inhibition of the rate of Factor Xa formation by a mixture of inhibitory peptides 267–283 and 284–303. The inverse of the rate of Factor Xa formation by the extrinsic pathway activation complex is plotted as a function of peptide 267–283 concentration in the presence of constant concentrations of peptide 284–303 of 0 (closed circle), 25 (closed triangle) and 50 (closed square)uM.

DESCRIPTION OF A PREFERRED EMBODIMENT

Figure 2A:
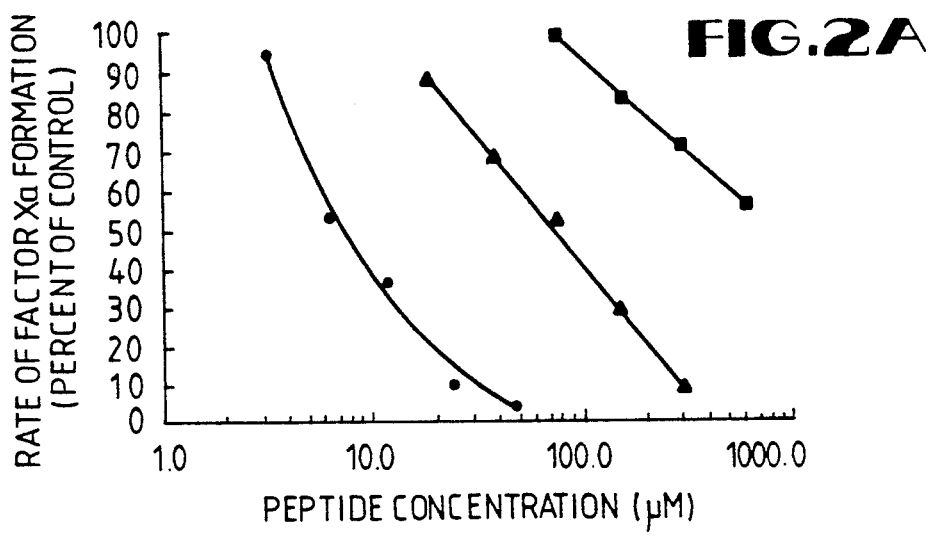
FIGS. 2A, 2B and 2C. Dose-dependent inhibition of the rate of Factor Xa formation initiated by the extrinsic, intrinsic, and RVV-X activation pathways. Components of each of the respective activation systems were combined in the presence of varying concentrations of peptide and incubated for 30 min at 37 degrees Centigrade. Factor X was added to initiate the reaction, and at various times, aliquots were removed and Factor Xa activity measured in an amidolytic assay. Data are plotted as a percentage of the rate determined in the absence of competing peptide versus the final concentrations of peptides 267–283 (circle); 284–303 (triangle) and 417–431 (square).

The present invention provides a number of novel anticoagulant peptides that are highly efficacious and specific. In addition, the peptides of the present invention are believed to be considerably less toxic than many anticoagulants used in the past. Finally, the peptides are not likely to induce undesirable immunologic side effects.

The coagulation inhibitory-peptides encompassed by the present invention are characterized by the ability to inhibit activation of Factor X or function of Factor Xa by at least about 40%, when tested using the chromogenic assays set forth herein. Furthermore, with the aid of the present disclosure, those of skill in the art may be able to devise additional assays suitable for determining percent inhibition of coagulation.

In a preferred embodiment, the coagulation-inhibitory peptides selectively inhibit activation of Factor X or function of Factor Xa. Moreover, although a number of peptides may exhibit the activity desired, the present inventor has shown that certain peptides are particularly effective. Accordingly, peptides corresponding to amino acids located at or around position 267–283 of the Factor X molecule using the numbering system set forth in Table 1 are preferred. Suitable peptides may comprise varying lengths, for example, from about 10 to about 35 amino acids, so long as they are capable of mediating the inhibition desired.

More specifically, the inventor has characterized at least 3 peptides representing the primary structure of Factor X that effectively inhibit the rate of Factor X activation and has discovered that the regions represented by these three peptides are involved in the association of Factor X with the activation complexes. This finding enables preparation of other effective peptide inhibitors that fall within the scope of the present invention. Therefore, although peptide 267–283, peptide 284–303, and peptide 417–431 all significantly inhibit the rate of Factor Xa formation in a dose-dependent manner and are preferred peptides for use in accordance with the present invention, a number of other peptides within the region extending from amino acid 237 to amino acid 303, may also be suitable anticoagulants.

The inventor has also characterized at least 7 Factor X peptides that effectively inhibit the function of Factor Xa by inhibiting the rate of thrombin formation by the Factor Xa:Factor Va complex. These peptides prevent the assembly of Factor Xa with Factor Va on the surface of phospholipid micelles or prevent the association of the substrate prothrombin from interacting with the assembled complex. Thus, these effective peptide inhibitors also fall within the scope of the present invention. Although peptide 211–222, peptide 237–262, peptide 254–269, peptide 267–283, peptide 284–303, peptide 363–375, and peptide 417–431 can inhibit factor Xa activity in a dose-dependent manner, other peptides of increased or decreased size may also be suitable to inhibit Factor Xa function.

In addition, it will be readily appreciated that the peptides set forth herein may be modified or derivatized in a variety of ways that will not significantly affect their anticoagulant function. Such modifications may include, for example, conservative amino acid substitutions, amino acid modifications (including, for example, amidation of the carboxyl terminus and acetylation of the amino terminus), conjugation of the peptide to a selected carrier molecule, or other alterations, such as deletion or addition of amino acids, that do not significantly affect the peptides' anticoagulant properties. Such modified peptides are considered to fall within the scope of the present invention.

The following example illustrates more clearly the method used by the present inventor to demonstrate the activity of a number of the peptides of the present invention using a model in vitro system. The second example illustrates a number of factors related to administration in vivo.

EXAMPLE I

DEMONSTRATION OF THE ACTIVITY OF THE PEPTIDES OF THE INVENTION IN IN VITRO SYSTEMS

A. Experimental Methods Used

1. Materials: Factor II (6), Factor IIa (7), Factor V (8), Factor VII/VIIa (9), Factor IX (10), Factor X (11), Factor Xa (12), and RVV-X (13) were isolated as previously reported. Factor IXa was produced from contact product (14) and isolated as previously described (12). Tissue Factor was prepared from human brain as described (15) and was kindly provided by Dr. James H. Morrissey (Research Institute of Scripps Clinic, La Jolla, A). Factor VIII was the generous gift of Dr. Michael Hrinda (Rorer Biotechnology, Inc., King of Prussia, Pa.). Glutaraldehyde (25%), cyanogen bromide, rabbit brain phospholipids (cephalin) and Factor VII/X deficient plasma were purchased from Sigma Chemical Company (St. Louis, Mo.). Chromozyme Xa was bought from Boehringer Mannheim Biochemicals (Indianapolis, Ind.), and S2338 was purchased from Helena Laboratories (Beaumont, Tex.). Protein A-agarose and papain-agarose were obtained from Pierce Chemical Company (Rockford, Ill.).

2. Peptide synthesis and characterization: Amino acid sequences corresponding to the primary structure of human Factor X, numbered according to Fung et al (16), are listed in Tables 1 and 1a. Selected peptides were modified by the addition of lysyl, tyrosyl or cysteinyl residues as indicated. Peptides were synthesized by an Applied Biosystems Peptide Synthesizer Model 430A according to the manufacture's protocols. Deblocking was performed with 30% trifluoroacetic acid in dichloromethane for 30 min. Cleavage and side chain protection was carried out in anhydrous hydrofluoric acid containing 20% anisole for 45 min at 0 degrees Centigrade.

All peptides were initially gel filtered on a Bio-Rad P-2 column (2.5×83 cm) equilibrated in 1% acetic acid. Subsequent analysis and purification was performed on a Perkin Elmer HPLC system using Vydac C4 (2.1×25 cm, 5 micron) columns equilibrated in 0.1% trifluoroacetic acid and developed with a linear gradient of 0–50% acetonitrile over 50 min. The compositions and concentrations of isolated peptides were determined by subjecting them to 24 hr. hydrolysis in 6 N HCl in evacuated tubes at 110 degrees Centigrade and by subsequent analysis on a Beckman Model 121M Amino Acid Analyzer (Beckman Instruments, Fullerton, Calif.).

TABLE 1

Effect of Synthetic Peptides on the Rate of Factor Xa Formation

| Peptide | Amino Acid Sequence | Factor Xa Formation (% of Control Rate) | | |
|---|---|---|---|---|
| | | Extrinsic | Intrinsic | RVVX |
| 82–89 | ELFTRKLC | 100 | 88 | 90 |
| 101–109 | HEEQNSVVC | 100 | 108 | 69 |
| 111–124 | CARGYTLADNGKAC | 83 | 121 | 77 |
| 130–139 | YPCGKQTLER | 94 | 94 | 100 |
| 162–187 | PYDAADLDPTENPFDLLDFNQTQPER | 67 | 100 | 68 |
| *195–210 + K | IVGGQECKDGECPWQA(K) | 88 | 98 | 76 |
| 211–222 | LLINEENEGFGG | 67 | 90 | 69 |
| 222–233 | GGTILSEFYILT | 87 | NT | 76 |
| 237–262 | CLYQAKRFKVRVGDRNTEQEEGGEAV | 72 | 40 | 63 |

TABLE 1-continued

Effect of Synthetic Peptides on the Rate of Factor Xa Formation

| Peptide | Amino Acid Sequence | Factor Xa Formation (% of Control Rate) | | |
|---|---|---|---|---|
| | | Extrinsic | Intrinsic | RVVX |
| 238-259 + K | LYQAKRF*EGDRNTEQEEGG(K) | 100 | 71 | 100 |
| 253-270 | TEQE*GGEAVHEVEVVIK | 100 | 91 | 71 |
| 267-283 | VVIKHNRFTKETYDFDI | 2 | 0 | 4 |
| 284-303 | AVLRLKTPITFRMNVAPACL | 19 | 0 | 34 |
| Y + 305-320 | (Y)ERDWAESTLMTQKTGI | 67 | 89 | 69 |
| Y + 325-338 | (Y)GRTHEKGRQSTRLK | 68 | 85 | 71 |
| 332-344 + K | RQSTRLKMLEVPY(K) | 67 | 101 | 104 |
| 344-362 | YVDRNSCKLSSSFIITQNM | 63 | 68 | 75 |
| 363-375 | FCAGYDTKQEDAC | 61 | 68 | 83 |
| 384-394 | VTRFKDTYFVT | 100 | 72 | 85 |
| 404-414 | ARKGKYGIYTK | 78 | 98 | 76 |
| 417-431 | AFLKWIDRSMKTRGL | 48 | 37 | 56 |

Rates of Factor Xa generation were determined by chromogenic assays in reaction systems containing purified proteins and using 1 mg/ml (0.29-1.11 mM) of each of the synthetic peptides. At these concentrations, each peptide was at $10^3$-$10^4$ molar excess over the substrate Factor X. Amino acid sequences are numbered according to Fung et al (16). K and Y in parenthesis are residues added to the indicated peptides; * = deleted amino acids; NT = not tested.

TABLE 1a

The Effect of Synthetic Peptides Representing Factor X on the Rate of Thrombin Formation

| Peptide | Amino Acid Sequence | Thrombin Formation (% of Control Rate) |
|---|---|---|
| 82-89 | ELFTRKLC | 115 |
| 101-109 | HEEQNSVVC | 116 |
| 111-124 | CARGYTLADNGKAC | 100 |
| 130-139 | YPCGKQTLER | 115 |
| 162-187 | PYDAADLDPTENPFDLLDFNQTQPER | 99 |
| 195-210 + K | IVGGQECKDGECPWQA(K) | 99 |
| 211-222 | LLINEENEGFGG | 32 |
| 222-233 | GGTILSEFYILT | 96 |
| 237-262 | CLYQAKRFKVRVGDRNTEQEEGGEAV | 34 |
| 238-259 + K | LYQAKRF*EGDRNTEQEEGG(K) | 98 |
| 254-269 | EQEEGGEAVHEVEVVI | 0 |
| 267-283 | VVIKHNRFTKETYDFDI | 0 |
| 284-303 | AVLRLKTPITFRMNVAPACL | 0 |
| Y + 305-320 | (Y)ERDWAESTLMTQKTGI | 93 |
| Y + 325-338 | (Y)GRTHEKGRQSTRLK | 100 |
| 332-344 + K | RQSTRLKMLEVPY(K) | 90 |
| 344-362 | YVDRNSCKLSSSFIITQNM | 79 |
| 363-375 | FCAGYDTKQEDAC | 59 |
| 384-394 | VTRFKDTYFVT | 100 |
| 404-414 | ARKGKYGIYTK | 88 |
| 417-431 | AFLKWIDRSMKTRGL | 24 |

Rate of thrombin formation were determined by amdolytic assays in reaction mixtures containing purified proteins and using 200 μM final concentrations of each of the synthetic peptides. The values are relative to reactions conducted in the absence of added peptide. At these concentrations each peptide was at $10^3$ to $10^4$ molar excess over the substratee factor X. Amino acid sequences are number according to Fung et al. (16). K and Y in parenthesis are residues added to the indicated peptides; * = deleted amino acids.

3. Kinetic Assays a. Rate of Factor X Activation: The effect of the synthetic peptides on the rate of activation of Factor X and prothrombin were analyzed in purified systems employing chromogenic assays. For the extrinsic activation complex, 20 ul each of tissue factor (2%), Factor VII/VIIa (1.5 nM) and CaCl$_2$ (40 mM) were added to 120 ul of peptide diluted in buffer (0.02 M Tris-HCl, 0.15 M NaCl, pH 7.4 containing 1 mg/ml bovine serum albumin; TBS-BSA). After incubation for 30 min at 37 degrees Centigrade, the reaction was started with the addition of 20 ul of Factor X (170 nM). For activation of Factor X by the intrinsic activation complex, 20 ul each of Factor IXa (5.4 nM), CaCl$_2$ (100 mM), cephalin (10x), Factor VIII (10 U/ml) were incubated with 100 ul of peptide in TBS-BSA at 37 degrees Centigrade for 30 min before the addition of 20 ul of Factor X (425 nM). Activation by RVV-X was determined by combining 40 ul of RVV-X (0.56 nM) with 4 ul of 500 mM CaCl$_2$ and 100 ul of peptide in TBS-BSA for 30 min at 0 degrees Centigrade, after which 100 ul Factor X (25 nM) was added to initiate the reaction.

b. Rate of Thrombin Formation: The ability of the synthetic peptides to inhibit Factor Xa function was assessed by their capacity to impede the rate of thrombin formation using a purified system and employing a specific thrombin chromogenic substrate. To 10 ul of Factor V (1.5 nM) was added 10 ul of phospholipid vesicles (30 uM), 3.3 ul of CaCl$_2$ (100 mM) and 57 ul of TBS-BSA or synthetic peptide. The mixture was incubated at 37 degrees Centigrade for 15 minutes, after which 20 ul of Factor Xa (12 pM) and prothrombin (0.35 uM) were added to initiate the reaction.

At defined time intervals from initiation of either reaction (a) or (b), 20 ul aliquots were removed and added to a microtiter plate containing 80 ul of 50 mM Tris-HCl, 225 mM NaCl, 10 mM EDTA, pH 8.2. After sample collection, 50 ul of 0.45 mM Chromozyme Xa (factor Xa chromogenic substrate) or 0.2 mM S-2238

(thrombin chromogenic substrate) was added, and the rate of change in absorbance at 405 nm was monitored for 8 min using a $V_{max}$ Kinetic Microplate Reader (Molecular Devices, Inc., Palo Alto, Calif.). The rate of Factor Xa or thrombin formation was calculated from the slope of linear regressions of data plotted as a function of the initial rate of hydrolysis (OD 405/min) versus time and expressed as OD 405/min/min.

4. Coagulation Assays: The effect of the synthetic peptide and antibodies to them on Factor X coagulation activity was determined using two-stage clotting assays specific for Factor X activation by the intrinsic, extrinsic, and RVV-X activation enzyme complexes.

For determination of extrinsic activation of Factor X, 50 ul of bovine Factor VII/X deficient plasma was added 50 ul each of 1.5 nM Factor VII/VIIa, 1% tissue factor, 25 mM CaCl$_2$, and peptide in TBS-BSA. Following incubation for 30 min at 37 degrees Centigrade, coagulation was initiated by the addition of 50 ul of 200 nM of Factor X, and the time for clot formation was measured. To determine the intrinsic activation of Factor X, 50 ul of human plasma immunochemically depleted of Factor X was combined with 50 ul each of cephalin containing 10 mg/ml kaolin, peptide in TBS-BSA and 50 mM CaCl$_2$ and incubated at 37 degrees Centigrade for 30 min. Factor X (50 ul of 105 nM) was added to initiate the reaction and the time for clot formation measured. RVV-X mediated activation of Factor X was achieved by mixing 50 ul of 1.1 nM RVV-X with 50 ul each of Factor X depleted plasma, peptide in TBS-BSA, and 30 mM CaCl$_2$ for 30 min at 37 degrees Centigrade. Factor X and Xa activity was measured by the addition of 50 ul of 25 nM Factor X and the time for clot formation determined.

The effect of synthetic peptides on prothrombin activation was determined in a two-stage coagulation assay. To 50 ul of Factor X depleted plasma was added 50 ul each of defined phospholipid vesicles (30 uM), CaCl$_2$ (15 mM) and peptide diluted in TBS-BSA. Following incubation for 15 minutes at 37 degrees Centigrade, coagulation was initiated by the addition of 50 ul of Factor Xa (250 pM) and the time for clot formation was measured.

Factor X and Xa activity was quantitated in the absence of added synthetic peptides from standard curves of the log of the dilution of normal human plasma versus the log of the clotting time. One unit of Factor X activity was defined as the activity present in 1 ml of pooled normal human plasma.

6. Inhibition Assays: The inhibition of Factor VII:tissue factor-, Factor IXa:Factor VIII-, and RVV-X-mediated activation of Factor X and inhibition of prothrombin cleavage by selected peptides was determined in the two-stage chromogenic assays described above. The peptides were initially screened at 0.3 to 1.1 mM added concentration. To determine the concentration of peptide required to inhibit 50% (CI$_{50}$) of the rate of Factor X or prothrombin activation, peptides at various concentrations or buffer (TBS-BSA) were incubated with their respective complexes. Following the addition of Factor X or prothrombin, the rate of Factor Xa or thrombin generation was determined and the percent of Factor X or prothrombin activation in the presence of different concentrations of peptide relative to buffer controls was calculated. Analogous determinations of the CI$_{50}$ values were measured in each of the specific coagulation assays outlined above. Factor X/Xa activity in the presence of varying concentrations of peptide was measured by comparing the clotting times to a standard curve constructed from the log of the clot time versus the log of Factor X concentration in the same incubation mixtures lacking peptides. Semi-logarithmic plots were used to calculate the CI$_{50}$ values by plotting the log of the concentration of peptide versus either the percentage of the rate of Factor Xa formation or of Factor X coagulant activity.

Kinetic analysis of multiple inhibitors known to be noncompetitive in nature was conducted holding the concentration of a first inhibitory peptide constant and varying the concentration of a second inhibitory peptide (17). For these studies, the inventor used the extrinsic activation complex at the component concentrations indicated above. The analysis for mutual exclusivity of the inhibitor peptide employed the following equations adapted from Segel (17):

$$\frac{1}{v} = \frac{\left[1 + \frac{aK_m}{[X]}\right]}{aK_iV_{max}}[I] +$$

$$\frac{1}{V_{max}}\left[1 + \frac{K_m}{[X]} + \frac{[J]}{bK_j} + \frac{K_m[J]}{[X]K_j}\right]$$

$$\frac{1}{v} = \frac{\left[1 + \frac{bK_m}{[X]}\right]}{bK_jV_{max}}[J] +$$

$$\frac{1}{V_{max}}\left[1 + \frac{K_m}{[X]} + \frac{[I]}{aK_i} + \frac{K_m[I]}{[X]K_i}\right]$$

where, $K_m$ = apparent dissociation constant for Factor X; [X], [I] and [J] = concentrations of Factor X; peptide i; and peptide j, respectively; $K_i$ and $K_j$ = apparent inhibitory constants for peptides i and j, respectively; and a and b interaction factors for peptide i and j, respectively.

7. Preparation, Characterization and Purification of Polyclonal Antibodies: Antibodies were raised against selected synthetic peptides coupled to keyhole limpet hemocyanin. Equivalent masses of peptide and carrier protein were mixed and incubated in 20 mM phosphate, 150 mM NaCl, pH 7.2, (PBS) containing 0.075% glutaraldehyde at room temperature for 16 hr. Following dialysis (using 1000 M$_r$ cutoff dialysis tubing) against 100 volumes of PBS with one change, equal volumes of the peptide-carrier conjugate (300 ug/150 ul) and Freund's complete adjuvant were emulsified and injected intradermally into 4 sites in the back, one site above each limb. After two weeks, the conjugate was emulsified in Freund's incomplete adjuvant and the injections repeated subcutaneously. The animals were challenged every month thereafter and sera were collected weekly starting 6 weeks after the initial immunization. Sera were tested for reactivity against Factor X and the free peptides using a solid phase radioimmunoassay. Polystyrene microtiter plates were coated with the peptide or Factor X at 2.5 ug/ml concentration by incubating each well with 100 ul of the peptide or protein in PBS for 16–18 hr at 4 degrees Centigrade. The plates were washed 3 times with PBS containing 0.5% Tween-20, 1 unit/ml aprotinin, 10 mg/ml BSA and 0.2% NaN$_3$ (SPRIA buffer). Non-specific protein binding sites were blocked by adding 1% (v/v) BSA in PBS for 30 min at room temperature. After removal of this solution, 100 ul of rabbit non-immune or specific antiserum serially diluted in SPRIA buffer was added for 90 min at 37 degrees Centigrade. Following incubation, the solution was removed, and the wells were washed three times with SPRIA buffer and incubated with 100 ul $^{125}$I goat anti-rabbit IgG (0.1 ug/ml) for 90 min at 37 degrees Centigrade. The unbound radioactivity was removed, the plates were washed with SPRIA buffer and dried, and the wells were cut out and counted in a gamma counter.

Purification of IgG from rabbit antisera was achieved by affinity chromatography on protein A-agarose. Equal volumes of rabbit antiserum and 100 mM Tris-HCl, 2 M NaCl, 0.1% NaN$_3$, pH 9.0, were mixed and applied to 12 ml Protein A-agarose column. The column was washed with four column volumes of 50 mM Tris-HCl, 1 M NaCl, 0.05% NaN , pH 9.0 and the bound IgG was eluted with two column volumes of 100 mM glycine-HCl, pH 3.0. Protein was monitored by absorbance at 280 nm and the IgG concentrations determined from the extinction coefficient of 13.5 (18). Specific antibodies were purified by passing the IgG fraction over a 25 ml column of Factor X coupled to agarose (2 mg/ml) by the CNBr activation method (19). Antibody was eluted by 2 M NH$_4$SCN, dialyzed extensively against TBS (pH 7.5), and concentrated by ultrafiltration using an Amicon P-10 membrane.

For selected studies, monovalent Fab fragments were prepared by papain digestion of the specific antibody. To each milligram of IgG in 20 mM sodium phosphate, 10 mM EDTA and 20 mM cysteine (pH 7.0) was mixed with 50 ul of papain-beads and incubated for 5 hr at 37 degrees Centigrade with constant agitation. After centrifugation to remove the insoluble enzyme, the supernatant was applied to a Protein A-agarose column-equilibrated in 10 mM Tris-HCl (pH 7.5). The column was washed with 10 mM Tris buffer and the unbound portion containing the Fab fragment was quantiated assuming an extinction coefficient of 13.5 (18).

B. Analysis of inhibition of Factor X activation by three activation pathways measured with the kinetic chromogenic assay Factor X can be activated by the extrinsic activation complex (factor VIIa:tissue factor), the intrinsic activation complex (factor IXa:factor VIIIa) and by an enzyme from Russell's viper venom (RVV-X). The peptides of the present invention were tested for their ability to inhibit Factor X activation caused by each pathway using the kinetic chromogenic assay described in sections A(3) and A(5) above. The assay was optimized by titrating components of each activating reaction to ensure that the activating proteases of the extrinsic and intrinsic pathways were in excess relative to their respective non-proteolytic cofactors and that the rates of Factor Xa formation were linear over the 8 min sampling period. The Factor X substrate was titrated against the preformed activation complexes in the presence of $10^3$-$10^4$ molar excess of each peptide. The peptides were incubated with each of the activating complexes for 30 min at 37 degrees Centigrade before the addition of Factor X (from 5.25 to 84 nM final concentration). Preliminary experiments indicated that this time was sufficient for peptide binding to come to equilibrium with the complexes. A hyperbolic increase in the rate of Factor Xa generation was observed as a function of substrate concentration in the absence and presence of the synthetic peptides.

FIG. 1 shows that peptide 267-283 inhibited the rate and extent of Factor X activation by the extrinsic activation complex by at least 90%. In contrast, Factor X activation was only slightly affected (approximately 20%) by peptide 253-270. Similar results were obtained using the other two activators of Factor X. In control experiments using DIP-factor Xa, the rate of Factor X activation was not affected by its product. A concentration of Factor X that was at or below the Km of the reaction was used in the additional studies described below.

Twenty-one synthetic peptides were assayed for their ability to inhibit the rate of Factor Xa generation by the extrinsic, intrinsic, and RVV-X activation complexes. In these experiments, each activation complex was assembled in the presence of 0.29-1.1 mM peptide for 30 min at 37 degrees Centigrade. Factor X was then added, and the rate of Factor Xa formation was determined (Table 1). Two peptides (267-283 and 284-303) nearly completely inhibited Factor X activation by each of the three activation complexes tested. Although two other peptides (237-262 and 417-431) showed partial inhibition, (affecting the intrinsic pathway to a greater extent than the RVV-X or the extrinsic pathway), the 237-262 peptide did not produce inhibition that was clearly dose-dependent.

Figure 2B:
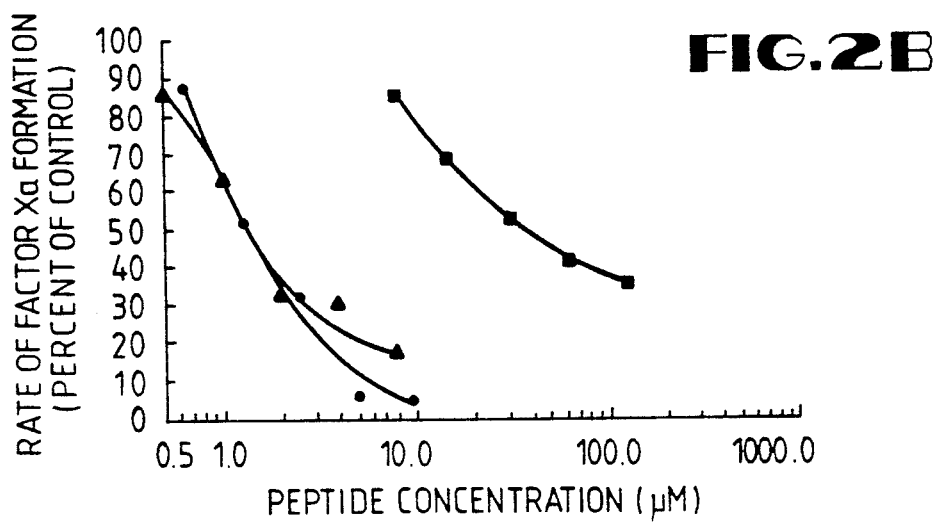
Figure 2C:
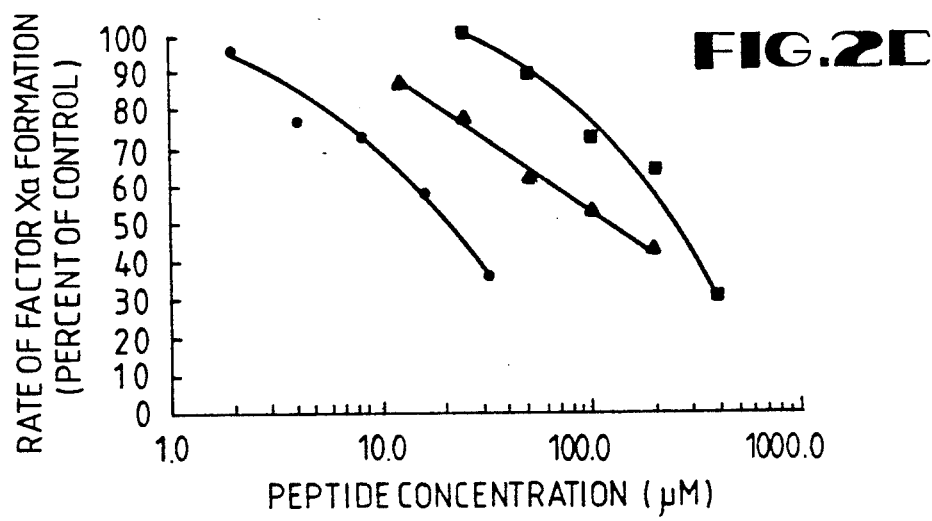

Additional experiments established that the inhibition mediated by the other three peptides was dose-dependent. Varying concentrations of peptide 267-283, peptide 284-303, or peptide 417-431 were incubated with each of the activation complexes and the rate of Factor Xa generation was analyzed (FIGS. 2A-2C). For each peptide, a dose-dependent inhibition was observed with each of the three activation complexes tested; however, the relative potency of the peptides differed. With the extrinsic and RVV-X pathways, the concentration of peptide 267-283 required for 50% inhibition (CI$_{50}$) of the rate of Factor Xa generation was at least 5 to 10-fold less than that required to achieve the same degree of inhibition with the other peptides tested. However, with the intrinsic pathway, the CI$_{50}$ for peptides 267-283 and peptide 284-303 were similar. The relative inhibitory activity of the peptides was as follows: Peptide 267-283 was an extremely potent inhibitor; peptide 284-303 was somewhat less potent; and peptide 417-431, was significantly inhibitory but less potent than either of the other two peptides.(Table 2).

TABLE 2

Summary of the Inhibition of the Rate of Factor Xa formation and Factor X Coagulant Activity by Synthetic Peptides
Concentration for 50% Inhibition (uM)$^a$

| Peptide | Rate of Factor Xa Formation | | | Coagulant Activity | | |
|---|---|---|---|---|---|---|
| | Extrinsic | Intrinsic | RVV.X | Extrinsic | Intrinsic | RVV.X |
| 267-283 | 8.4 | 1.4 | 19 | 23 | 28 | 60 |
| 284-303 | 78 | 1.7 | 104 | >500 | 46 | 14 |

TABLE 2-continued

Summary of the Inhibition of the Rate of Factor Xa formation
and Factor X Coagulant Activity by Synthetic Peptides
Concentration for 50% Inhibition (uM)[a]

| Peptide | Rate of Factor Xa Formation | | | Coagulant Activity | | |
|---|---|---|---|---|---|---|
| | Extrinsic | Intrinsic | RVV.X | Extrinsic | Intrinsic | RVV.X |
| 417–431 | >500 | 35 | 208 | >500 | >500 | 20 |

[a]The concentration of peptide which inhibited 50% of the rate of Factor Xa formation or the Factor X coagulant activity is indicated.

The inhibition was specific; control peptides with but synthesized in reverse order failed to inhibit the three activation reactions. The intrinsic activation complex appeared to be the most sensitive to peptide inhibition; the $CI_{50}$ of peptides 267-283 and 284-303 was below 5 uM. However, with each activation complex tested, the relative inhibitory potency of the three peptides was similar. This finding suggests that a common substrate recognition site may be involved in all three activation pathways. Possibly, the 267-283 sequence contains a principle substrate recognition domain, whereas the other two peptides expressed secondary recognition sites or comprised a partial but physiologically active recognition sequence. Peptide 284-303 was nearly as potent as peptide 267-283 in inhibiting the intrinsic activation complex; this region may play a more selective role in directing activation of Factor X by the intrinsic pathway.

Figure 3A:
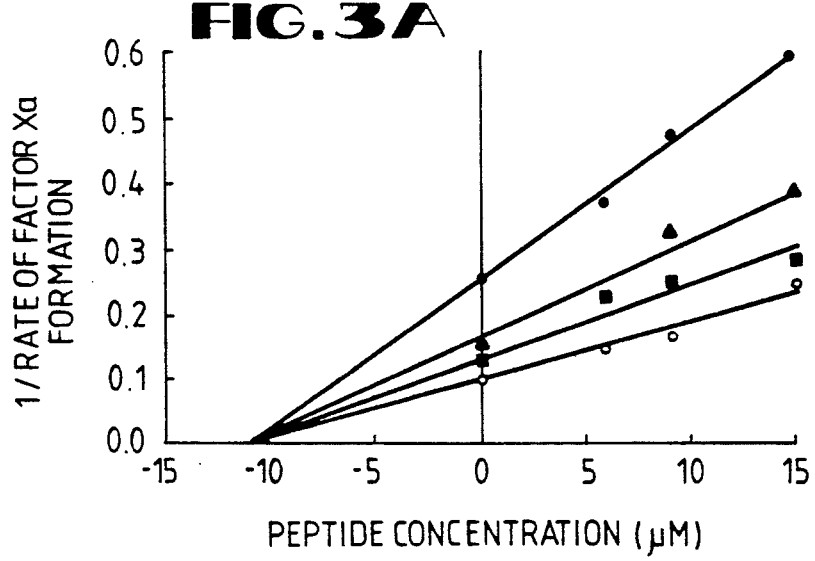
FIGS. 3A, 3B and 3C. Dixon plots of the inhibition of the rate of activation of Factor X by synthetic peptides 267–283, 284–303 and 417–431. The inverse of the rate of Factor Xa formation by the extrinsic activation complex (OD 405/min/min) is plotted as a function of the final peptide concentrations at Factor X concentrations of 0.169 (closed circle), 0.33 (closed triangle), 0.50 (closed square), 0.67 (open circle) and 0.84 (open triangle)uM.
Figure 3B:
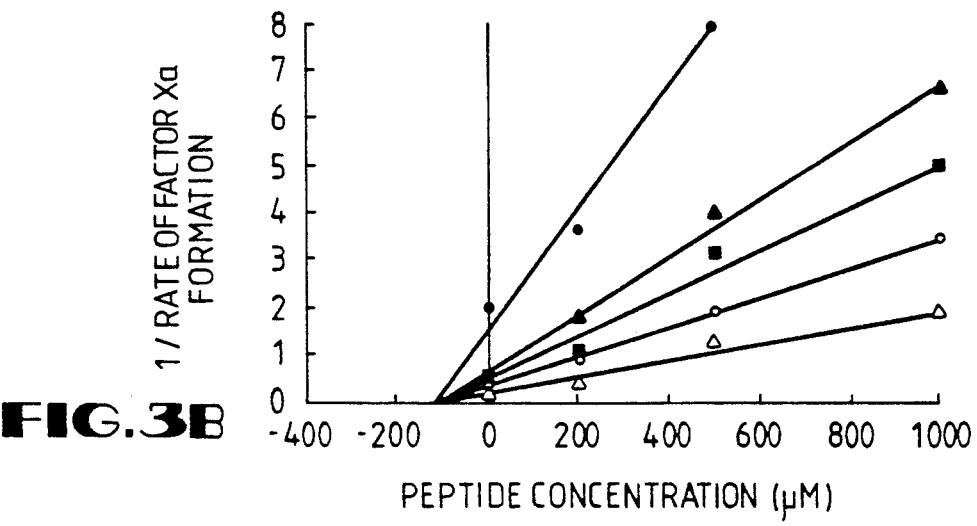
Figure 3C:
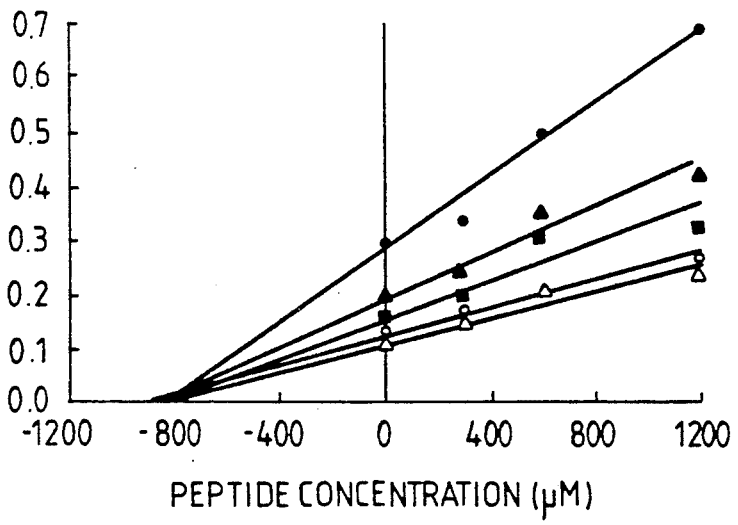

The rate of Factor Xa formation was then measured at different concentrations of Factor X and varying concentrations of the inhibitory peptides in order to determine whether the peptides interacted directly with the active site of the activators or acted at a distal site. The Dixon plots in FIGS. 3A-3C show peptide-mediated inhibition of extrinsic activation complex. For each peptide, plots of the inverse reaction rate versus the final peptide concentration produced linear regression lines that intersected on the abscissa. These results are consistent with a noncompetitive mode of inhibition. Noncompetitive inhibition was also observed when the peptides were analyzed using each of the other two activation complexes. The apparent inhibition constant (Ki) observed for each peptide differed significantly; the Ki of peptide 267-283 was 11.0 uM; the Ki of peptide 284-303 was 73.6 uM; and the Ki for peptide 417-431 was 1055 uM. (Table 3).

TABLE 3

Peptide Inhibition Constants for Factor X Activation

| | Ki (uM)[a] | | |
|---|---|---|---|
| Peptide | Extrinsic | Intrinsic | RVV-X |
| 267–283 | 11.0 ± 2.19 | 2.99 ± 1.84 | 8.69 ± 2.20 |
| 284–303 | 73.6 ± 7.79 | 3.05 ± 1.77 | 123 ± 23.9 |
| 417–431 | 1055 ± 144 | 39.7 ± 14.0 | 361 ± 56.4 |

[a] Ki values were determined from Dixon plots of the rate of Factor Xa generation initiated by the extrinsic, intrinsic and RVV-X activation pathways. At least four concentrations of Factor X were used and the Ki values are expressed as the mean ± SD for 4 to 5 determinations.

These results indicate that the peptides do not directly interact with the active site of the three activators, but act at distal sites. The interactions may impede the association of a given activator with Factor X, or alternatively, may induce a conformational change in the activator which affects its ability to cleave the substrate.

Additional experiments were performed in order to determine whether the inhibition mediated by each peptide was additive. Concentrations of peptides which individually gave about 50% inhibition were used alone or in combination with the other peptides. The peptides were incubated with the components of the extrinsic activation complex for 30 min at 37 degrees Centigrade. With combinations of two or three peptides, the rate of Factor Xa formation was reduced to an extent that was not synergistic but approached the predicted inhibition attributed to the individual peptides. (Table 4).

TABLE 4

The Effect of Mixtures of Inhibitory Peptides on the Rate of Factor Xa Formation

| | Factor X Activation (% Control) | | | |
|---|---|---|---|---|
| | Experiment #1 | | Experiment #2 | |
| Peptides Tested | Observed | Predicted | Observed | Predicted |
| 267–283 (6 uM)[a] | 42.0 | — | 58.0 | — |
| 284–303 (60 uM) | 35.0 | — | 47.8 | — |
| 417–431 (600 uM) | 41.9 | — | 52.0 | — |
| 267–283 + 284–303 | 16.0 | 14.7 | 21.5 | 27.7 |
| 284–303 + 417–431 | 25.5 | 14.7 | 33.0 | 24.9 |
| 267–283 + 417–431 | 24.4 | 17.6 | 24.0 | 30.2 |
| 267–283 + 284–303 + 417–431 | 7.5 | 6.2 | 10.8 | 14.4 |

[a]Peptides 267-283, 284-303 and 417-431 were assayed using the extrinsic activation pathway at the final concentrations indicated in the parenthesis. Values are expressed as the percent activity of the rate of Factor Xa generation relative to the rate measured in the absence of peptide. Predicted values are based on the products of the remaining Factor X activity of the individual peptides.

Because each noncompetitive inhibitory peptide appeared to prevent the activation of Factor X completely, the inventor repeated the analysis using a constant concentration of peptide 284-303 and varying concentrations of peptide 267-283. Dixon plots of the results of these experiments are shown in FIG. 4. The slopes of the linear regression lines were similar and independent of the fixed concentration of peptide 284-303, indicating that the two inhibitors were mutually exclusive of one another. Analogous results were seen with the other mixtures of inhibitory peptides.

These results indicate that the three peptides do not act in a synergistic or additive manner, but rather exhibit mutual exclusivity to one another (17). The data also suggest that association of Factor X with an activator is mediated by simultaneous interactions with at least three distinct regions on Factor X located distally from its cleavage site.

C. Peptide mediated inhibition of Factor Xa activation as assayed in coagulation assays.

Figure 5A:
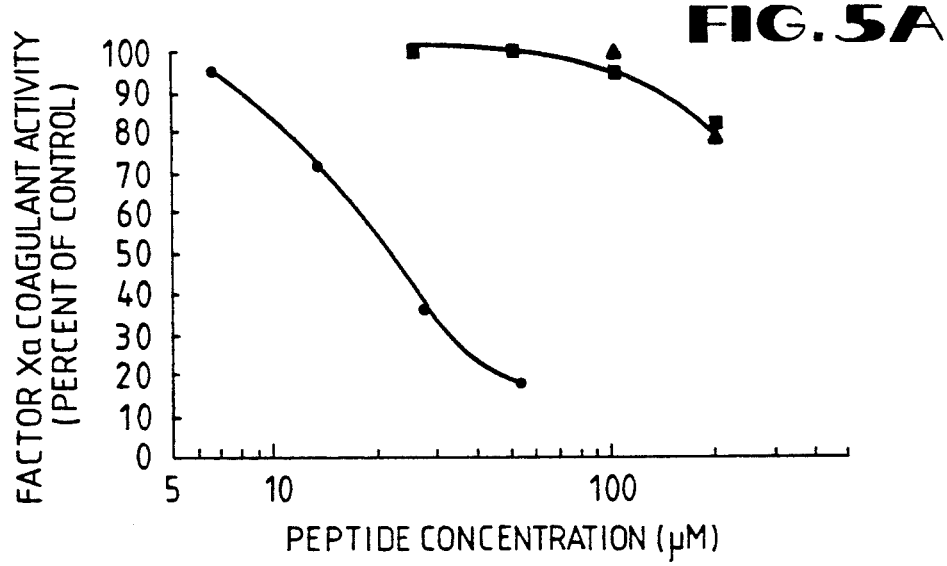
FIGS. 5A, 5B and 5C. Dose-dependent inhibition of Factor X coagulant activity initiated by the extrinsic, intrinsic, and RVV-X activation pathways. Deficient plasma and the appropriate purified components of each respective complex were mixed with increasing concentrations of peptide for 30 min at 37 degrees Centigrade. Purified Factor X was added and the time for clot formation determined. Percent activity was determined from clotting times in the absence of added peptides and employing standard curves constructed from the log of the clot time versus the log of the concentrations of Factor X. The relative Factor X activity is plotted as a function of the concentration for synthetic peptides 267–283 (closed circle), 284–303 (closed triangle) and 417–431 (closed square).
Figure 5B:
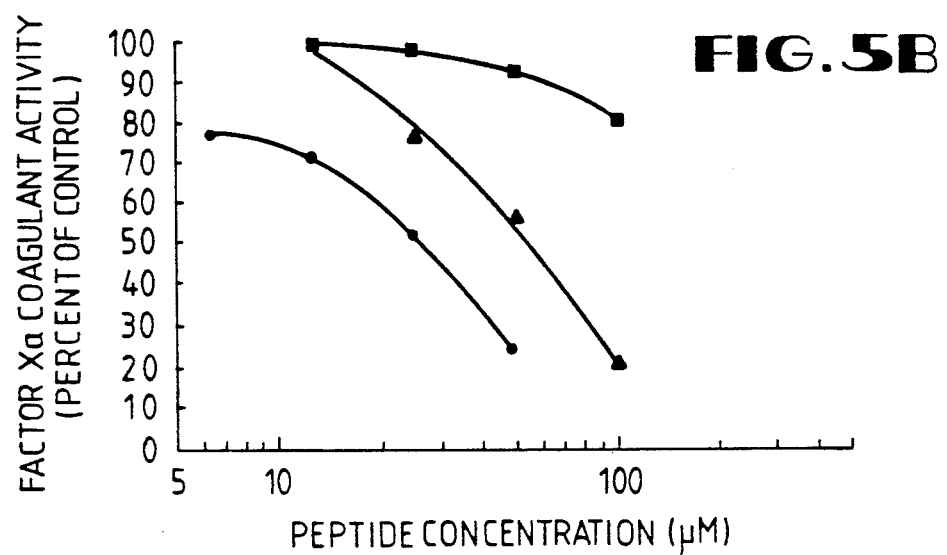
Figure 5C:
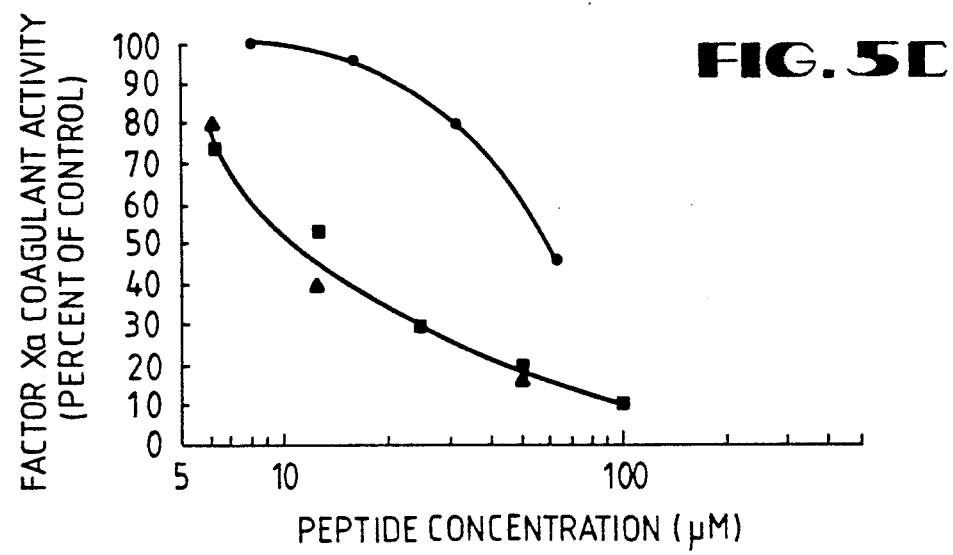

The three peptides described above were also tested for their ability to inhibit Factor X coagulant activity in a clot formation assay. In these experiments, peptide 267–283 inhibited Factor X coagulant activity with each of three activation complexes tested with 50% inhibition occurring at a peptide concentration of about 23–60 uM. Peptide 284–303 inhibited Factor X coagulant activity initiated by the intrinsic- and RVV-X-activation complexes but was a less potent inhibitor of extrinsic pathway-mediated Factor X coagulant activity. Peptide 417–431 did not inhibit the Factor X coagulant activity initiated by the either the intrinsic or extrinsic pathway, but was a very effective inhibitor of the RVV-X pathway (FIGS. 5A–5C). A summary of the apparent $CI_{50}$ values for these peptides in the three coagulation assays is presented in Table 2, supra.

The $CI_{50}$ values of the peptides were generally higher when analyzed by coagulation reaction than when assayed using the kinetic chromogenic assay. The 267–283 peptide appeared to be the best inhibitor in the extrinsic and intrinsic coagulation assays, but 3 to 20-fold more peptide was required to achieve 50% inhibition than was required when inhibition was measured using the chromogenic assay. However, with the exception of the RVV-X activator, the relative potency of the peptides observed in the coagulation based assays was similar to that observed with the chromogenic assay systems.

The reason for these differences is not completely understood. However, because coagulation assays are technically complex and involve two additional reactions before the end point is reached, the sensitivity of the assays may be compromised. Alternatively plasma-derived peptidase or nonspecific adsorption of the peptides to plasma proteins may decrease the effective peptide concentration.

Moreover, as indicated above, in the RVV-X coagulation assay peptide 284–303 and peptide 417–431 were better inhibitors than peptide 267–283. Activation of Factor X by RVV-X occurs in solution, whereas activation of Factor X by both the intrinsic and extrinsic pathways is membrane-mediated. Because the synthetic peptides do not bind to phospholipid membranes, their ability to inhibit fluid-phase Factor X activation or a subsequent reaction may be greater than their ability to inhibit surface-directed reactions where the effective concentration of procoagulant reactants might be higher (20–23). Further, the 5 to 10-fold greater sensitivity of peptides 284–303 and 417–431 in the RVV-X initiated coagulation assay relative to the kinetic assay implicates these regions in subsequent association within the prothrombinase complex.

D. Antibody-mediated inhibition of Factor X activation measured by chromogenic and coagulation-based assays To further demonstrate that the inhibitory synthetic peptides represent important regions of interactions for Factor X, the inventor raised polyclonal antibodies to the three inhibitory peptides and confirmed their specificity by showing that each antiserum bound only to its respective immunizing peptide when assayed by solid phase radioimmunoassays. The antibodies were purified by immunoaffinity chromatography on a Factor X-agarose column, and, in some cases, Fab fragments prepared as described in Section A, above.

Figure 6A:
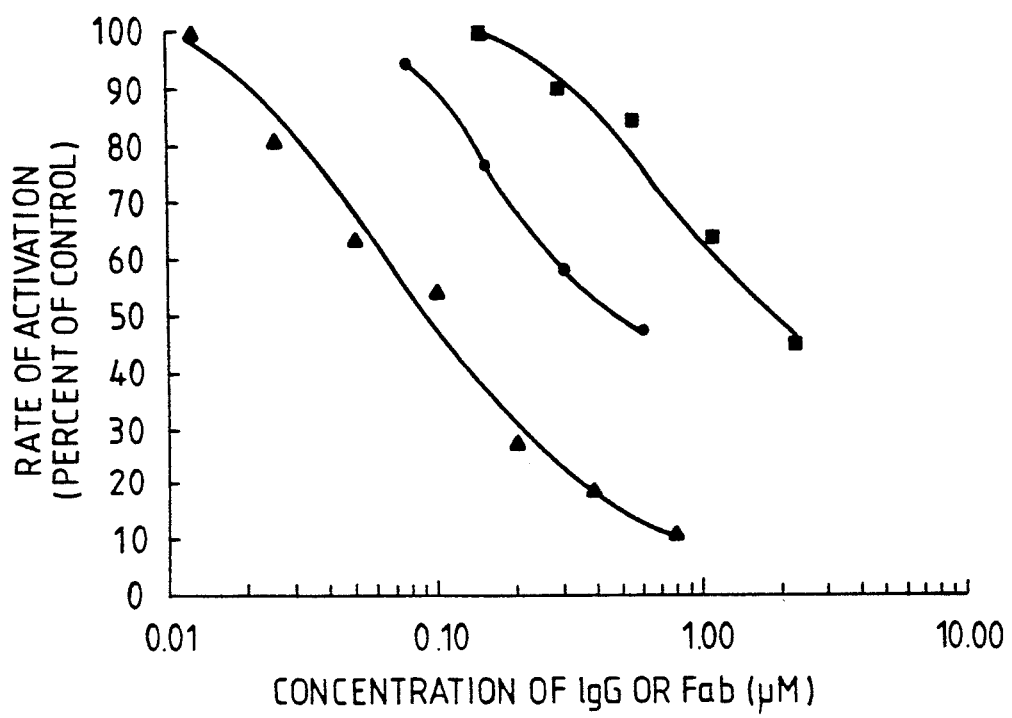
FIGS. 6A and 6B. Antibody inhibition of Factor X activation. Rabbit antibodies raised to peptides 267–283, 284–303, and 417–431 were affinity purified on a Factor X-agarose column and incubated with Factor X for 15 min at 37 degrees Centigrade before assay. Top: the ability of increasing concentrations of the Fab fragment from anti-peptide 267–283 antibody to inhibit the rate of Factor X activation initiated by the extrinsic (closed circle), intrinsic (closed triangle), or RVV-X (closed square) activation initiated by the extrinsic (closed circle), intrinsic (closed triangle), or RVV-X (closed square) activation complexes. Bottom: neutralization of Factor X coagulant activity initiated by the extrinsic pathway following incubation with the antibodies to peptide 267–283 (closed circle), 284–303 (closed triangle), and 417–431 (closed square). All values are relative to activities observed in the presence of non-immune rabbit IgG.

The Fab fragments were assayed for the ability to inhibit the rate of Factor X activation generated by each of the three activation pathways described above. Fab fragments specific for peptide 267–283 inhibited the rate of Factor X activation by the extrinsic, intrinsic, and RVV-X activation complexes with apparent $CI_{50}$ concentrations of 4.0, 0.9 and 17 uM, respectively (FIG. 6A, top). Similar results were seen when the Fab fragments of antibodies specific for the peptides 284–303 and peptides 417–431 were used (data not shown).

Figure 6B:
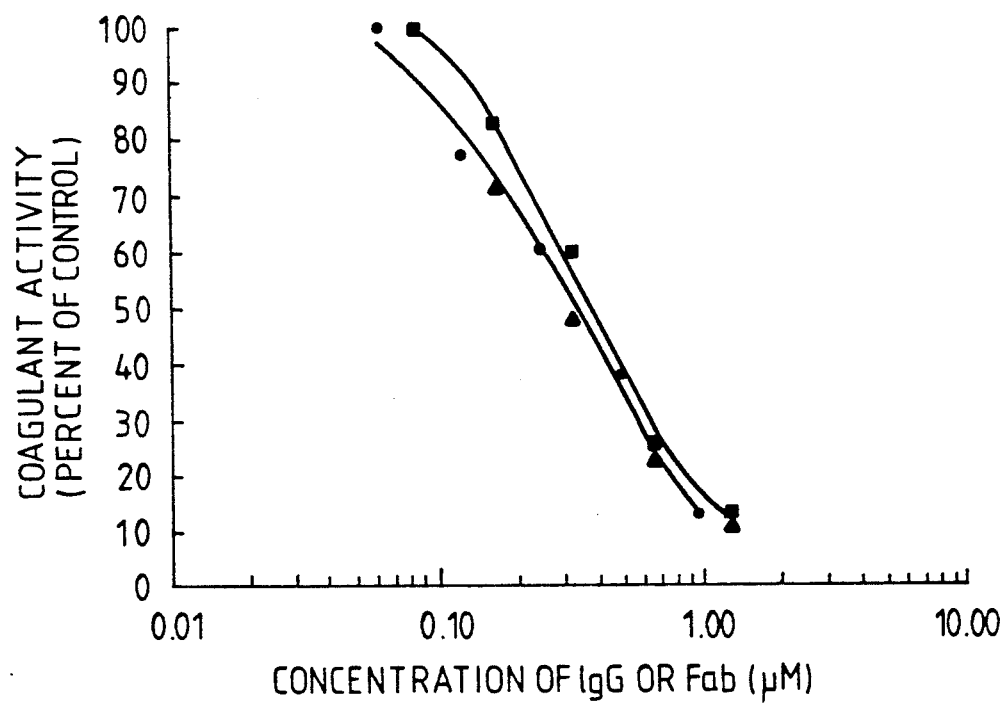

IgG preparations specific for each of the three peptides also inhibited extrinsic pathway-mediated Factor X coagulant activity in a dose-dependent manner. The estimated $CI_{50}$ concentrations were 0.3, 0.3, and 0.4 uM for antibodies to peptides 267–283, 284–303, and 417–431, respectively (FIG. 6B bottom). Analogous results were observed when the antibodies were tested in coagulation assays initiated by the intrinsic and RVV-X complexes (data not shown). Normal rabbit IgG failed to inhibit or neutralize the activation of Factor X assessed in either the chromogenic or coagulation assays.

The fact that the anti-peptide antibodies could be affinity purified on Factor X-agarose columns indicates that the regions represented by these peptides are exposed and available for interaction with other molecular species at the solvent accessible surface of Factor X. Peptide 267–283 and peptide 417–431 are hydrophilic; the 284–303 sequence is less so. Although hydrophilicity and surface accessibility may correlate in some cases (24–25), not all parts of an epitope need follow these guides (26–27). When antibodies to peptides 267–283, 284–303, or 417–431 were reacted with Factor X, they were all capable of inhibiting the rate of Factor Xa formation as monitored by both the chromogenic and the coagulation-based assays. However, because IgG has three times the mass of Factor X, it may have caused steric interference in these assays. Indeed, Fab fragments ($M_r=50,000$) of the anti-peptide 267–283 antibody showed a differential ability to inhibit Factor X activation when the activation systems were assayed by chromogenic assay, a finding suggesting that the epitopes recognized by the antibody are in close proximity to the sequence mediating the intrinsic activation complex interaction and distal to that region recognized by RVV-X.

The fact that antibodies made to these three inhibitory peptides can react with Factor X and affect its activation supports the notion that the regions on Factor X represented by these amino acid sequences are largely surface-exposed and are readily available to interact with other proteins including the antigen combining sites of Fab fragments or IgG molecules (28). The finding that the three peptides inhibit the activation of Factor X by a noncompetitive mechanism also supports the theory that the sites recognized by the activators of Factor X are located distal to the potential cleavage site and therefore away from the active site of the enzyme within the extrinsic, intrinsic and RVV-X activation complexes.

When comparing the location of the inhibitory peptide sequences of factor X relative to the three-dimensional structure of chymotrypsin (29,30), one sees that the three regions are located close to one another on the surface of the molecule. The 267-283 sequence includes the potential active site aspartic acid (Asp$^{282}$) extending to the amino terminus and is homologous to the 89-103 sequence in chymotrypsinogen containing active site Asp$^{102}$. The 284-303 region of factor X (chymotrypsinogen sequence 104-116) is located to the carboxyl side of this aspartic acid residue; and the factor X 417-431 sequence (chymotrypsinogen sequence 229-243) is located within the carboxyl terminus of the molecule. When viewing the three-dimensional structure of chymotrypsinogen relative to its Arg$^{15}$-Ile$^{16}$ cleavage site (31) with the assumption that the Arg$^{194}$-Ile$^{195}$ of factor X is spatially located similarly, the three sequences are found on the surface of the protein opposite to that of the cleavage site. The inventor's finding that the three peptides inhibit the activation of factor X by a noncompetitive mechanism supports the concept that the sites recognized by the activators of factor X are located distal to the potential cleavage site and therefore away from the active site of the enzyme within the extrinsic, intrinsic and RVV-X activation complexes.

The three specific activators of Factor X probably have sufficient surface area to allow for binding at a recognition site on the substrate and permit alignment of their respective active sites to the potential Arg$^{194}$-Ile$^{195}$ cleavage site on Factor X. The largest activator is the intrinsic complex which is composed of Factor IXa (46,000 $M_r$; ref 32) and Factor VIIIa (~166,000 $M_r$; ref 33). The extrinsic activation complex, composed of Factor VIIa (48,000 $M_r$; ref 34) and Tissue Factor (30,000 $M_r$; refs 35-36), has a similar total mass as RVV-X (79,000 $M_r$; ref 13). Of course, the minimal mass requirement for specific activation of Factor X may be less (37).

Figure 7:
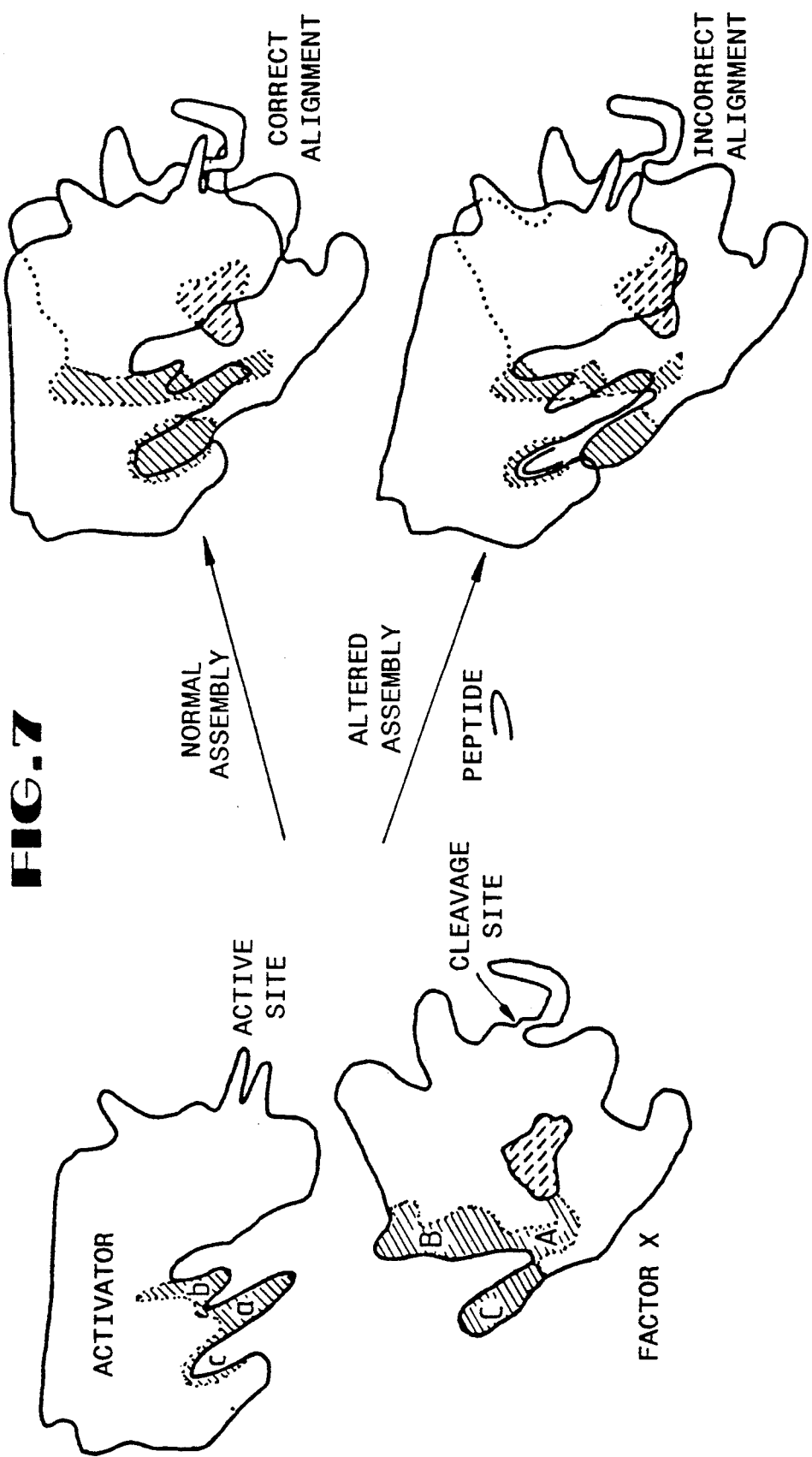
FIG. 7. Hypothetical alignment of Factor X activators through a multiple loci recognition unit. Factor X is depicted as having a minimum of three regions which comprise the recognition unit on its surface where A, B, and C represents the approximate location of amino acids 267–283, 284–303, and 417–431, respectively. The activator of Factor X is indicated as having corresponding complementary sites of interaction indicated as a, b, and c. When Factor X and its activator associate, the three loci in the recognition unit align the activator in the proper orientation, brining the active site adjacent to the cleave site in Factor X. In the presence of a peptide inhibitor (peptide C), the binding site in the activator is occupied, thereby interfering with the orientation of the activator on the surface of Factor X and resulting in misalignment of the activator and failure to cleave the substrate.

From the examples set forth above, it is possible to construct a model of a multifoci binding site on the surface of Factor X which is recognized by the extrinsic and intrinsic activation complex as well as by RVV-X. Binding of Factor X to this site could properly align the active sites of these activators in the correct orientation for cleavage and activation of Factor X. FIG. 7 depict a schematic of recognition unit which localizes the three inhibitory peptides on Factor X. It is proposed that there are an equal number of complementary regions on the activates which combine with Factor X at these points. Because there are a minimum of three association sites (with the potential of several additional regions of interaction), there is a highly ordered alignment of the activator with the substrate which brings its active site into close proximity to the Arg$^{194}$-Ile$^{195}$ cleavage site on the zymogen. Inhibition of Factor X activation observed by the synthetic peptides may interfere with optimal binding of the activator resulting in a misalignment of the active site to the potential cleavage site.

E. ANALYSIS OF INHIBITION OF FACTOR Xa FUNCTION

Factor Xa associates with activated Factor Va on a phospholipid surface in the presence of calcium. A chromogenic assay was used to investigate the ability of the panel of synthetic peptides to inhibit the activation of prothrombin by Factor Xa. In preliminary experiments it was determined that similar results were obtained whether prothrombin was added before or after factor Xa and that the 15 minute incubation period was sufficient for the peptide-protein interactions to reach equilibrium. Table 1a summarizes the inhibition of prothrombin activation in the presence of 200 uM of each peptide. Seven peptides prevented thrombin formation by greater than 40% when compared to reactions containing buffer only. These peptides represented the amino acid sequences 211-222, 237-262, 254-269, 267-283, 284-303, 363-375, 417-431. Thus, a limited number of synthetic peptides representing the primary structure of Factor Xa could inhibit this reaction and these were analyzed further.

Figure 8A:
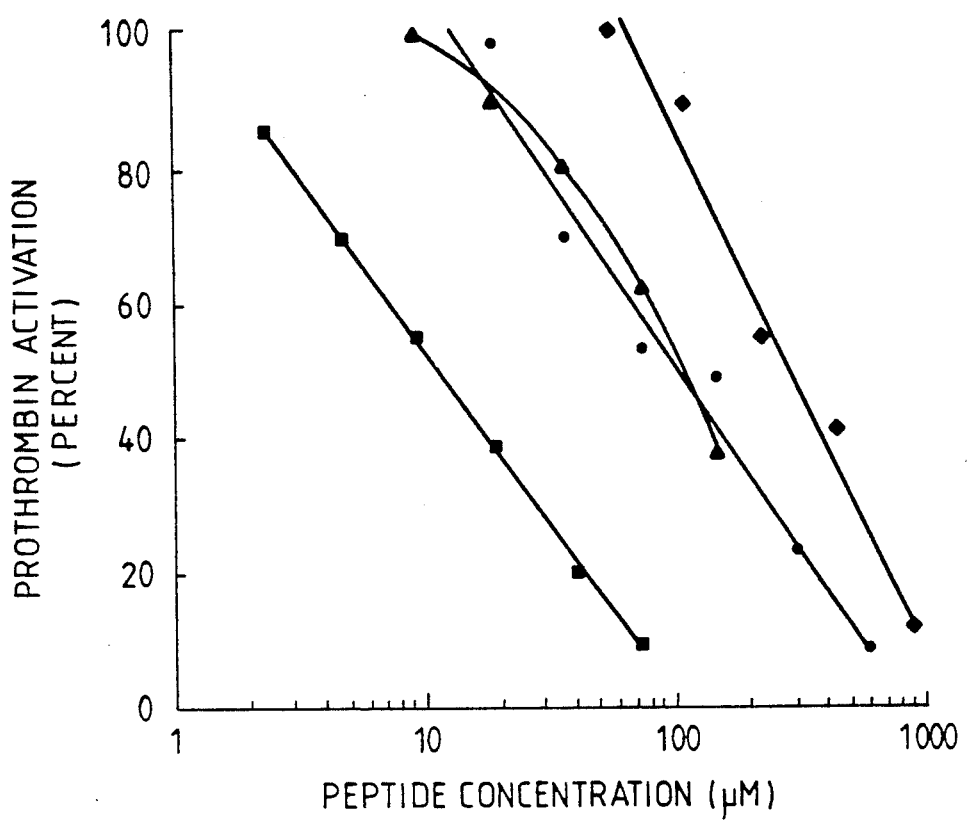
FIGS. 8A and 8B. Dose-dependent inhibition of Factor Xa Function. Factor Va, phospholipid and calcium were incubated with varying concentrations of synthetic peptide and incubated for 15 minutes at 37 degrees Centigrade. Factor Xa and prothrombin were added to initiate the reaction, and at various times, aliquiaots were removed and thrombin activity measured in a chromogenic assay. Data are plotted as a percentage of the rate of prothrombin activation versus the final concentrations of peptides 211–222 (closed circle), 237–263 (closed triangle), 284–303 (closed square), and 363–375 (closed diamond) in the upper panel and peptides 254–269 (closed circle), 267–283 (closed triangle) and 417–431 (closed square) in the lower panel.
Figure 8B:
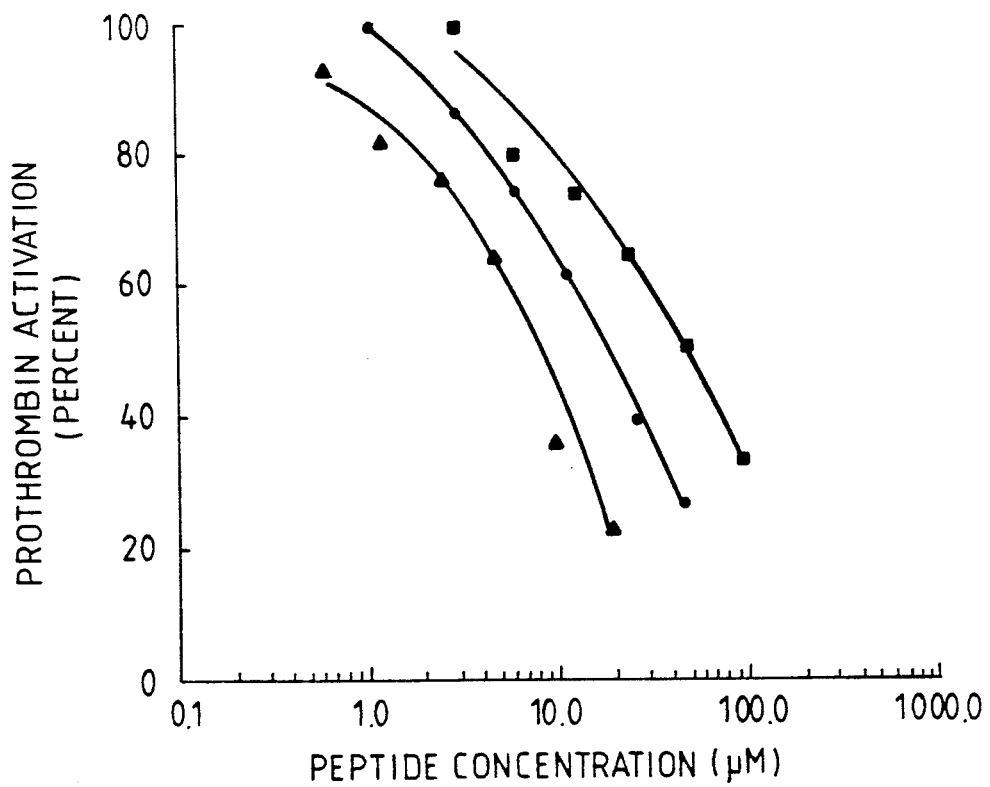

The dose-dependent inhibition of each synthetic peptide was next determined. Varying concentrations of each peptide were incubated with the Factor Va, phospholipid and calcium mixtures, and the rate of prothrombin activation determined following the addition of prothrombin and Factor Xa. FIGS. 8A-8B depicts the profiles of each of the seven inhibiting peptides. In every case, dose-dependency was observed indicating that each of these regions Factor Xa participated in the molecular interactions resulting in the activation of prothrombin.

Figure 9A:
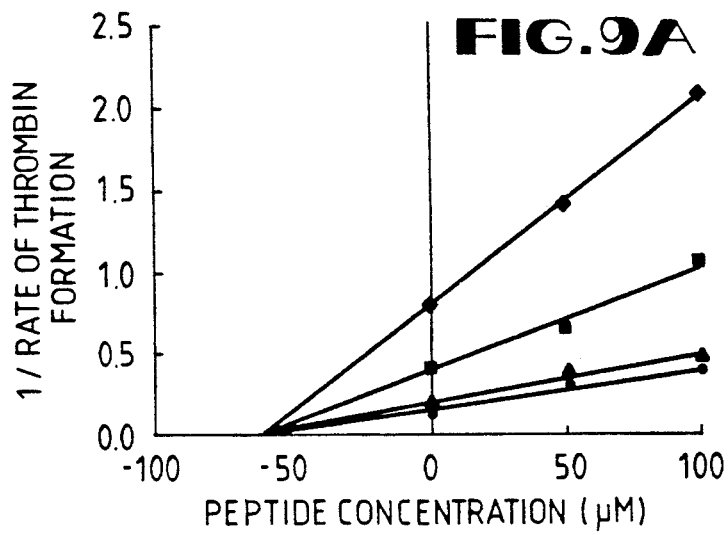
FIGS. 9A, 9B and 9C. Dixon plots of the inhibition of the rate of activation of prothrombin by synthetic peptides 211–222, 363–375 and 417–431. The inverse of the rate of thrombin formation is plotted as a function of the final peptide concentration at prothrombin concentrations of 4.35 (circle), 8.7 (triangle), 17.5 (square) and (diamond) nM.
Figure 9B:
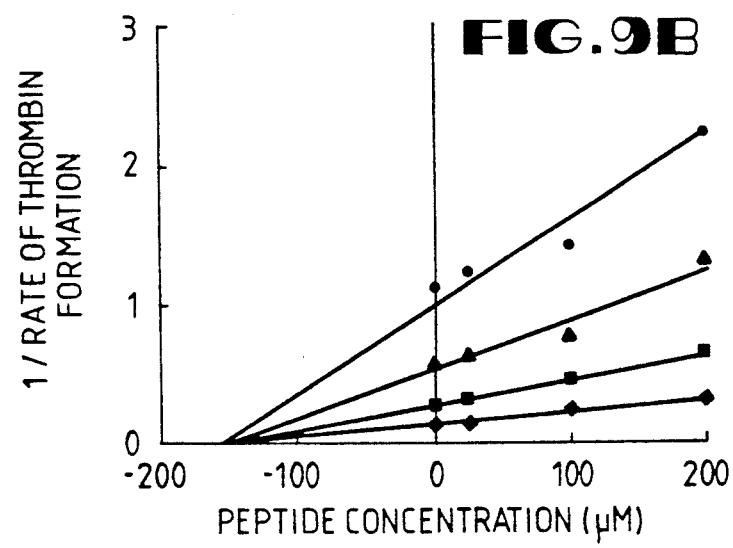
Figure 9C:
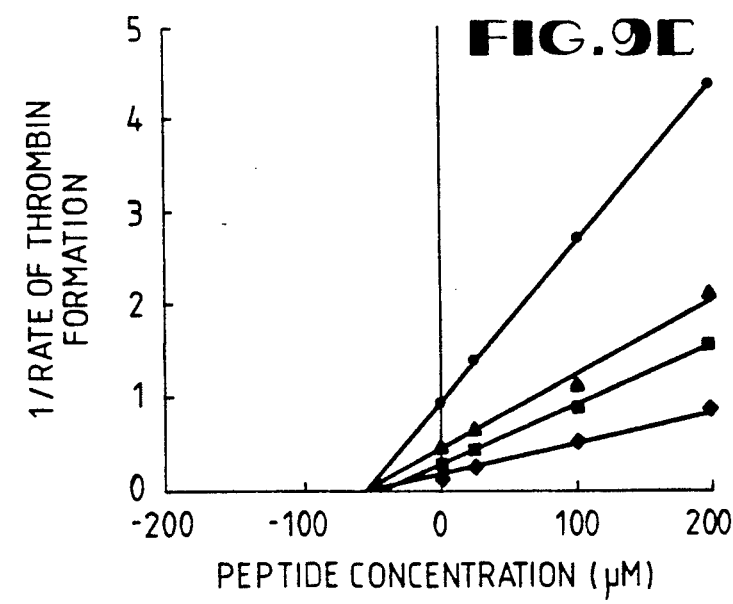

The type of inhibition was also explored by varying the peptide concentrations in the presence of differing amounts of prothrombin. FIGS. 9A-9C summarizes data for three of the six peptides investigated. Linear regression lines intersected the abscissa indicating noncompetitive inhibition. These data suggests that regions on Factor Xa distal to the active site mediate the interaction between the prothrombinase complex and prothrombin. A summary of the inhibitor constants ($K_i$) for this reaction are presented in Table 5. Both peptides 267-283 and 284-303 were the best inhibitors of this reaction, followed by peptide 417-431 > peptide 211-222 > peptide 237-262 > peptide 363-375. Interestingly, the most potent peptides were the same peptides which inhibited factor X activation.

TABLE 5

| Peptide Inhibition Constants for Factor Xa Function | |
| --- | --- |
| Peptide | $K_i$ (uM) |
| 211-222 | 67.2 ± 9.49 |
| 237-262 | 134 ± 27.3 |
| 254-269 | NT |
| 267-283 | 16.3 ± 3.43 |
| 284-303 | 16.2 ± 4.54 |
| 363-375 | 150 ± 8.44 |
| 417-431 | 48.8 ± 5.53 |

$K_i$ values were determined in assays varying the substrate prothrombin. NT = not tested.

Figure 10A:
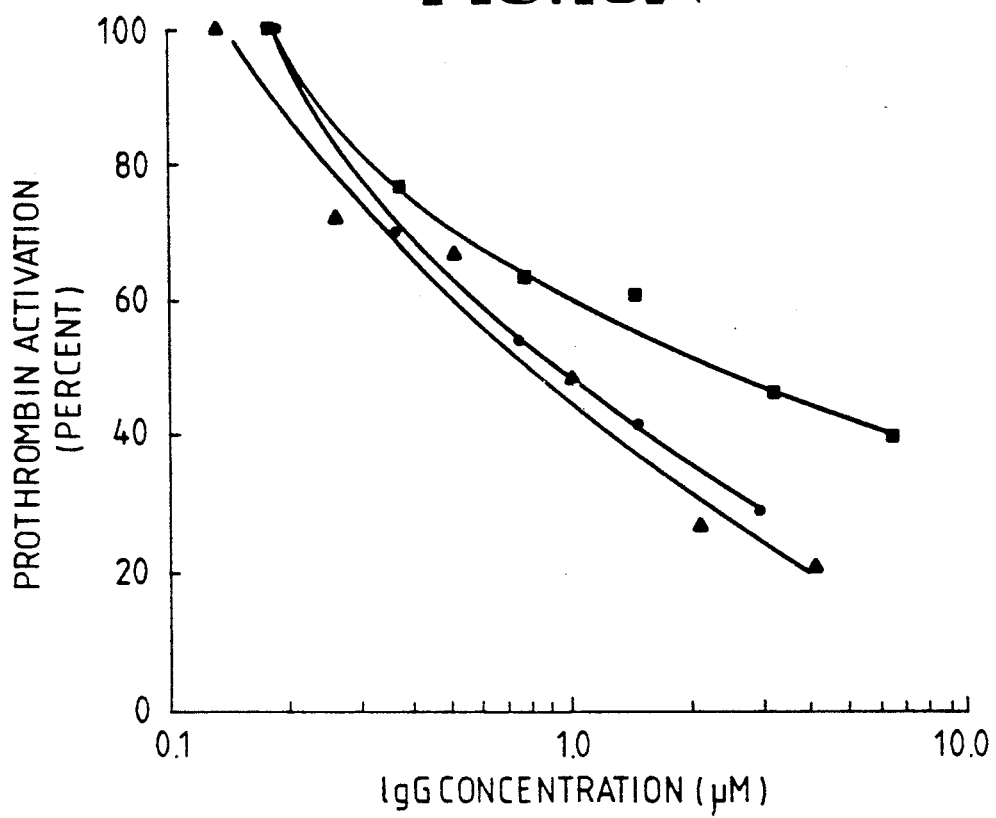
FIGS. 10A and 10B. Antibody inhibition of Factor Xa function. Rabbit antibodies raised to peptides 237–262 (square), 267–283 (circle) and 284–303 (triangle) in the upper panel and to peptides 211–222 (triangle) and 417–431 (circle) in the lower panel were affinity purified on Factor X-agarose columns. Varying concentrations of each antibody were incubated with factor Xa (40 pM) for 15 minutes at 37 degrees Centigrade and the remaining Factor Xa activity was determined by measuring the rate of prothrombin activation employing the thrombin specific S-2238 chromogenic substrate.
Figure 10B:
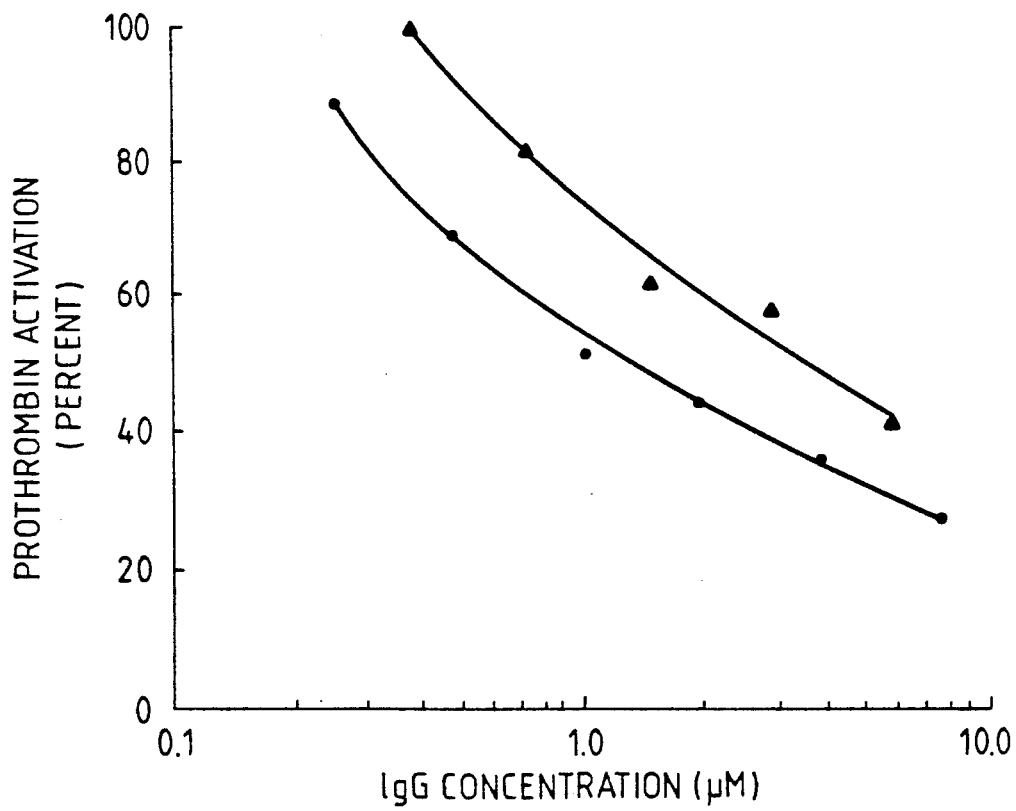

To confirm that the these regions participated in prothrombinase assembly and function, rabbit antibodies prepared against selected peptides were immunoaffinity purified on factor X-agarose columns and tested for their ability to prevent prothrombin activation. Factor Xa was incubated with varying concentrations of antibody for 15 minutes at 37 degrees Centigrade before assay. FIGS. 10A-10B depicts the dose-dependent inhibition of prothrombin formation as a function of antibody concentration. All of the antibodies inhibited this reaction at 50% within the range of 0.8 to 4 uM. Lower amounts of antibodies specific for peptides 267-283 and 284-303 were required for inhibition than those made to peptides 211-222, 237-262 and 417-431. It may be that these regions are more important for prothrombin activation than the others, but the size of the IgG molecules may cause stearic hinderance in these associations.

Thus, in addition to the three regions of Factor X which mediate its activation, there are four additional regions which are involved in the function of Factor Xa. Regions represented by peptides 267–283, 284–303 and 417–431 are in close spatial proximity to one another. Regions represented by peptides 211–222, 237–262, and 254–269 are located spatially close to one another forming a second recognition domain on the surface of Factor Xa and adjacent to the area defined by the first set on synthetic peptides involved with Factor X activation. It is possible that both regions are required for Factor Xa function, presumably by interacting with the cofactor, Factor Va. Additional studies will be required to determine if these peptides can physically associate with either Factor Va, prothrombin or both. The location of peptide 363–375 represents an area close to the binding pocket of serine proteases. The noncompetitive nature of this inhibitory peptide in this model is surprising; one would predict it's mechanism of inhibition should be competitive.

EXAMPLE II

USE OF THE PEPTIDES TO INHIBIT COAGULATION IN VIVO

Due to precautions necessarily attendant to development of every new pharmaceutical, the coagulation inhibitory peptides of the present invention have not yet been tested in a clinical setting in human subjects. Therefore, the in vitro activity of the peptides has been used to demonstrate the utility of the present invention; these assays are accepted by those in the art as reliable indicators of in vivo activity. The following prophetic embodiments represent the preferred mode presently contemplated by the present inventor for carrying out the practice of the invention in various clinical settings.

First, it is believed that the coagulation inhibitory peptides will prove to be useful in treating numerous diseases in which thrombotic disorders are involved. In particular, these include, but are not limited to deep vein thrombosis, pulmonary embolism, arterial thrombotic diseases including acute arterial occlusion, and disseminated intravascular coagulation.

For treatment, the coagulation inhibitory peptides may be formulated into pharmaceutical compositions and administered using a therapeutic regimen compatible with the particular formulation. As described further below, with the aid of the present disclosure, those of skill in the pharmaceutical and medical arts should be able to derive suitable dosages and schedules of administration for any of a number of effective compositions containing the anticoagulant peptides. Accordingly, pharmaceutical compositions within the scope of the invention include compositions where the active ingredient is contained in an effective amount to achieve its desired anticoagulant activity. However, a preferred dosage comprises that which is sufficient to achieve an effective blood concentration of about 3 to 40 uM of peptide which is equal to 6 to 80 $\mu$g/ml. Assumming 6L of blood in an average person, the total dosage would be 35–500 mg of peptide or for 150 kg human (0.25 to 3.2 mg/kg). Nevertheless, although a preferred range has been described, determination of the effective amounts for treatment of any particular patient or thrombotic disorder should be determined by those of skill in the art.

Although the most efficacious manner of administering the anticoagulant peptide will depend on the particular clinical situation, it is believed that in many cases the peptides may be most easily administered by formulating such with a suitable pharmaceutical excipient or vehicle and administering the formulation intravenously. Alternatively, the peptides may be formulated for intramuscular, subcutaneous, intradermal, or intraarticular injection; such injections might be used to treat pathologic conditions at these sites when thrombosis is involved.

In addition to the anticoagulant peptide compounds, the pharmaceutical compositions may contain any of a number of suitable excipients and auxiliaries that facilitate processing of the active compounds into preparations that can be used pharmaceutically. As indicated above, although the preparations will most commonly be designed for parenteral administration, compositions designed for oral or rectal administration are also considered to fall with the scope of the invention. Generally, preferred compositions will comprise from about 0.05% to 5.0% by weight of active ingredients.

Suitable formulations for parenteral administration include aqueous solutions of the active compounds in water-soluble or water dispersible form. In addition, in some cases, suspensions of the active compounds may be administered in suitable lipophilic carriers. The formulations may contain substances that increase viscosity, for example, sodium carboxymethyl cellulose, sorbitol, and/or dextran. Optionally, the formulation may also contain stabilizers.

With all of each formulations, suitable excipients, for example, saline lipids or physiologic buffers, are known to those of skill in the art and may be used. The foregoing description of the invention has been directed to particular preferred embodiments in accordance with the requirements of the patent statutes and for purposes of explanation and illustration. It will be apparent, however, to those skilled in the art that many modifications and changes may be made without departing from the scope and the spirit of the invention.

For example, the peptides may be modified from those disclosed herein in a number of particulars that do not significantly affect the anticoagulant activity. Such particulars may include, but are not limited to, conservative amino acid substitutions and modifications, including, for example, amidation of the carboxyl terminus, acetylation of the amino terminus, conjugation of the polypeptide to a physiologically inert carrier molecule, or other sequence alterations, such as deletion or addition a limited number of amino acids, so long as such changes do not significantly affect the peptide's anticoagulant properties. It is apparent that the invention may also be utilized with other suitable modifications within the state of the art. It is the Applicants intention in the following claims to cover all such equivalent modifications and variations which fall within the true spirit, and scope of the invention.

REFERENCES

The following references, a number of which are cited in ,#the text above by number, may prove useful for facilitating practice of certain aspects of the present invention and are incorporated herein by reference. Inclusion of a reference in this list is not intended to and does not constitute an admission that such reference constitutes prior art with respect to the present invention.

1. Jackson, C. M. (1984) *Prog. Hemost. Thromb.* 7:55–109

2. Greer, J. (1981) *J. of Mol. Biol.* 153:1027–1042

3. Furie, B. Being.D. H., Feldman R., Robison, D. J., Burnier, J. P., and Furie, B. C. (1982) *J. Biol. Chem.* 257:3875–3882

4. Hwett-Emmett, D., Czelusniak, J., and Goodman, M. (1981) *Ann. N.Y. Acad. Sci.* J70:511–527

5. Fujikawa, K., Goan, M., Legaz, M. E., and Davie E. W. (1974) *Biochemistry* 13:5290–5299

6. Schwartz, B. S., Levy, G. A., Curtiss, L. K., Fair, D. S., and Edgington, T. S. (1981) *J. Clin. Invest.* 67:1650–1658.

7. Fair, D. S., and Plow, E. F. (1986) *Thromb. Res.* 41:67–78

8. Dahlback, B. (1980) *J. Clin. Invest.* 66:583–591

9. Fair, D. S. (1983) *Blood* 6:784–791

10. Thompson, A. R. (1977) *J. Clin. Invest.* 5:900–910

11. Fair, D. S., Plow E. F., and Edgington, T. S. (1979) *J. Clin. Invest.* 64:884–894

12. Burri B. J., Edgington, T. S., and Fair, D. S. (1987) *Biochim. Biophys. Acta* 923:176.186

13. Kisiel,W., Hermodson, M. A., and Davie, E. W. (1976) *Biochemistry* 15:4901–4906

14. Nossel, H. L. (1964) *Thromb. Diath. Haemorrh.* 12:505–518

15. Morrissey, J. H., Revak D., Tejada, P., Fair D. S., and Edgington, T. S. (1988) *Thromb. Res.* 50:481–493

16. Fung, M. R., Hay, C. W., and MacGillivray. R. T. A. (1985) *Proc. Natl. Acad. Sci. USA* 82:3591–3595

17. Segel, I. R. (1975) *Enzyme Kinetics-Behavior and Analysis of Rapid Equilibrium and Steady-State Enzyme Systems.* pp 465–504 John Wiley & Sons, New York 18. Kirschenbaum, D. M. (1973) *Anal. Biochem.* 56:237–244

19. March, S. C., Parikh, I., and Cuatrecasas, P. (1974) *Anal. Biochem.* 60:149–152

20. Rosing, J., Tans, G., Govers-Riemslag, J. W., Zwaal, R. F., and Hemker, H. C. 980) *J. Biol. Chem.* 55:274–283

21. van Dieijn, G., Tans, G., Rosing J., and Hemker, H., (1981) *J. Biol. Chem.* 256:3433–3442

22. Nesheim. M. E., Eid S., and Mann, K. G. (1981) *J. Biol. Chem.* 256:9874–9882

23. Nesheim, M. E., Tracy P. B., and Mann, K. G. (1984) *J. Biol. Chem.* 5:1447–1453

24. Parker, J. M. R., Guo, D., and Hodges, R. S. (1986) *Biochemistry* 5, 5425–5432

25. Welling, G. W., Weijer, W. J., van der Zee, R., and Welling-Wester, S. (1985) *FEBS Lett.* 188:215–218

26. Berzofsky, J. A. (1985) *Science* 229:932–940

27. Dyson, H. J., Lerner, R. A., and Wright, P. E. (1988) *Ann. Rev. Biophys. Biophys. Chem.* 17:305–324

28. Novotny, J., Handschumacher, M., Haber, E., Bruccoleri, R. E., Carlson, W. B., Fanning D. W., Smith, J. A., and Rose, G. D. (1986) *Proc. Natl. Acad. Sci. USA* 83:226–230

29. Matthews, B. W., Sigler, P. B., Henderson, R., and Blow, D. M. (1967) *Nature* 14:652.656

30. Sigler, P. B., Blow, D. M., Matthews, B. W., and Henderson, R. (1968) *J. Mol. Biol.* 35:143–16426

31. Freer, S. T., Kraut, J., Robertus, J. D., Wright, H. T., and Xuong, N. H. (1970) *Biochemistry* [ ]1997–2009

32. DiScipio, R. G., Kurachi K., and Davie, E. W. (1978) *J. Clin. Invest.* 61:1528–1538

33. Eaton, D., Rodriguez, H., and Vehar, G. A. (1986) *Biochemistry* 5:505–512

34. Broze, G. J. Jr., and Majerus, P. W. (1980) *J. Biol. Chem.* 255:1221–1247

35. Morrissy, J. H., Fakhrai, H., and Edgington, T. S. (1987) *Cell* 50, 129–135

36. Spicer, E. K., Horton, R., Bloem, L., Bach, R., Williams, K. R., Guha, A., Kraus, J., Lin, T.N.C., Nemerson, Y. and Konigsberg, W. H. (1987) *Proc. Natl. Acad. Sci. USA* 84:5148–5152

37. Falanga, A., and Gordon, S. G. (1985) *Biochemistry* 24:5558–5567

What is claimed is:

1. A composition of matter, consisting essentially of a peptide of about 10–50 amino acids, said peptide having a sequence that is at least about 95% homologous to a sequence of from about 10–50 amino acids selected from the following sequence: E-Q-E-E-G-G-E-A-V-H-E-V-E-V-V-I-K-H-N-R-F-T--K-E-T-Y-D-F-D-I-A-V-L-R-L-K-T-P-I-T-F-R-M-N-V-A-P-A-C-L.

2. A composition of matter consisting essentially of peptide of about 15–35 amino acids, said peptide having a sequence that is at least about 95% homologous to a sequence of from about 15–35 amino acids selected from the following sequence: V-V-I-K-H-N-R-F-T-K-E-T-Y-D-F-D-I-A-V-L-R-L-K-T-P-I-T-F-R-M-N-V-A-P-A-C-L.

3. A composition of matter consisting essentially of a peptide of from about 14 to 20 amino acids characterized in that said peptide contains a stretch of amino acids exhibiting about at least 95% amino acid homology to a peptide sequence that is V-V-I-K-H-N-R-F-T-K-E-T-Y-D-F-D-I.

4. A composition of matter according to claim 3 where said peptide contains a stretch of amino acids having the sequence V-V-I-K-H-N-R-F-T-K-E-T-Y-D-F-D-I.

5. A composition of matter consisting essentially of a peptide of from about 14 to 20 amino acids characterized in that said peptide contains a stretch of amino acids exhibiting about 95% amino acid homology to a peptide sequence that is A-V-L-R-L-K-T-P-I-T-F-R-M-N-V-A-P-A-C-L.

6. A composition of matter according to claim 5 where peptide contains a stretch of amino acids having the sequence A-V-L-R-L-K-T-P-I-T-F-R-M-N-V-A-P-A-C-L.

7. A composition of matter consisting essentially of a peptide of from about 14–20 amino acids characterized in that said peptide contains a stretch of amino acids exhibiting about 95% amino acid homology to a peptide sequence that is A-F-L-K-W-I-D-R-S-M-K-T-R-G-L.

8. A composition of matter according to claim 7 where said peptide contains a stretch of amino acids having the sequence A-F-L-K-W-I-D-R-S-M-K-T-R-G-L.

9. A composition of matter consisting essentially of a peptide of from about 14–20 amino acids characterized in that said peptide contains a stretch of amino acids exhibiting about 95% amino acid homology to a peptide sequence that is T-E-Q-E-E-G-G-E-A-V-H-E-V-E-V-V-I-K.

10. A composition of matter according to claim 9 where said peptide contains a stretch of amino acids having the sequence T-E-Q-E-E-G-G-E-A-V-H-E-V-E-V-V-I-K.

11. A composition of matter consisting essentially of a peptide of from about 12 to about 20 amino acids characterized in that said peptide contains a stretch of amino acids exhibiting at least about 95% amino acid sequence homology to a peptide sequence that is L-L-I-N-E-E-N-E-G-F-G-G.

12. A composition according to claim 11 where said peptide contains a stretch of amino acids that is L-L-I-N-E-E-N-E-G-F-G-G.

13. A composition of matter consisting essentially of a peptide of from about 16 to about 30 amino acids characterized in that said peptide contains a stretch of amino acids exhibiting at least about 95% amino acid sequence homology to a peptide sequence that is C-L-Y-Q-A-K-R-F-K-V-R-V-G-D-R-N-T-E-Q-E-E-G-G-E-A-V.

14. A composition according to claim 13 where said peptide contains a stretch of peptides that is C-L-Y-Q-A-K-R-F-K-V-R-V-G-D-R-N-T-E-Q-E-E-G-G-E-A-V.

15. A composition of matter consisting essentially of a peptide of from about 14 to about 20 amino acids characterized in that said peptide contains a stretch of amino acids exhibiting at least about 95% amino acid sequence homology to a peptide sequence that is E-Q-E-E-G-G-E-A-V-H-E-V-E-V-V-I.

16. A composition of matter according to claim 15 where said peptide contains a stretch of amino acids that is E-Q-E-E-G-G-E-A-V-H-E-V-E-V-V-I.

17. A composition of matter consisting essentially of a peptide of from about 10 to 16 amino acids characterized in that said peptide contains a stretch of amino acids exhibiting about 95% amino acid sequence homology to a peptide sequence that is F-C-A-G-Y-T-D-K-Q-E-D-A-C.

18. A composition of matter according to claim 17 where said peptide contains a stretch of amino acids that is F-C-A-G-Y-T-D-K-Q-E-D-A-C.

19. A pharmaceutical formulation for the treatment of clotting disorders comprising the composition of any one of claims 3, 4, 5, 7, 9, 11, 13, 15, 17, together with a pharmaceutically acceptable vehicle.

* * * * *

UNITED STATES PATENT AND TRADEMARK OFFICE
CERTIFICATE OF CORRECTION

PATENT NO. : 5,187,155
DATED : February 16, 1993
INVENTOR(S) : Daryl S. Fair

It is certified that error appears in the above-indentified patent and that said Letters Patent is hereby corrected as shown below:

Column 1, Line 34, change "prvded" to --provided--.

Column 6, Line 6, change "brining" to --bringing--.

Column 13, Line 18, change "NaN" to --NaN$_3$--.

Column 15, Line 12, insert --similar net charge and a peptide corresponding to 267-283-- after "with".

Column 19, Line 47, change "activates" to --activators--.

Column 22, Line 60, delete ",#".

Col. 26, claim 19, line 18, delete "4", and insert --1, 2,-- before "3".

Signed and Sealed this

Seventh Day of December, 1993

*Attest:*

BRUCE LEHMAN

*Attesting Officer*  *Commissioner of Patents and Trademarks*